(12) United States Patent
Mesallum

(10) Patent No.: US 8,714,160 B2
(45) Date of Patent: *May 6, 2014

(54) METHOD AND APPARATUS FOR PERFORMING TRANSESOPHAGEAL CARDIOVASCULAR PROCEDURES

(71) Applicant: Microaccess Inc., Weston, MA (US)

(72) Inventor: Sameh Mesallum, Boston, MA (US)

(73) Assignee: Microaccess Inc., Quincy, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,202

(22) Filed: Dec. 17, 2012

(65) Prior Publication Data

US 2013/0103018 A1 Apr. 25, 2013

Related U.S. Application Data

(63) Continuation of application No. 13/310,548, filed on Dec. 2, 2011, now Pat. No. 8,475,378, which is a continuation of application No. 11/050,284, filed on Feb. 3, 2005, now Pat. No. 8,070,680, which is a continuation of application No. 10/700,113, filed on Nov. 3, 2003, now abandoned, which is a continuation of application No. 09/718,642, filed on Nov. 22, 2000, now Pat. No. 6,689,062.

(60) Provisional application No. 60/167,147, filed on Nov. 23, 1999.

(51) Int. Cl.
*A61B 19/00* (2006.01)

(52) U.S. Cl.
USPC .............................. 128/898; 600/104; 600/471

(58) Field of Classification Search
None
See application file for complete search history.

(56) References Cited

U.S. PATENT DOCUMENTS

| | | |
|---|---|---|
| 3,643,653 A | 2/1972 | Takahashi et al. |
| 3,760,810 A | 9/1973 | Van Hoorn |
| 3,853,117 A | 12/1974 | Murr |
| 4,103,680 A | 8/1978 | Yoon |
| 4,233,984 A | 11/1980 | Walling |
| 4,471,766 A | 9/1984 | Terayama |
| 4,671,295 A | 6/1987 | Abrams et al. |
| 4,735,194 A | 4/1988 | Stiegmann |
| 4,886,059 A | 12/1989 | Weber |
| 4,887,612 A | 12/1989 | Esser et al. |
| 4,976,717 A | 12/1990 | Boyle |
| 5,224,497 A | 7/1993 | Ehlers |
| 5,247,938 A | 9/1993 | Silverstein et al. |
| 5,297,536 A | 3/1994 | Wilk |
| 5,315,992 A | 5/1994 | Dalton |
| 5,382,231 A | 1/1995 | Shlain |

(Continued)

*Primary Examiner* — Unsu Jung
*Assistant Examiner* — Saurel J Slkin
(74) *Attorney, Agent, or Firm* — Lando & Anastasi LLP

(57) ABSTRACT

An apparatus for performing a transesophageal cardiovascular procedure includes an elongated tubular main access device having a first lumen with an open proximal end and a distal side opening, and a second lumen with a rigid outer wall and a collapsible inner wall. The second lumen is adapted to receive an elongated probe or surgical device. The apparatus further includes an inflatable sealing component on the outside of the main access device above and below the side opening, and a first fluid conduit extending along the main access device for inflating the sealing component so that when the main access device is inserted into a patient's esophagus and the sealing component is inflated. The portion of the esophagus opposite the side opening is isolated from the remainder of the esophagus above and below the side opening.

18 Claims, 14 Drawing Sheets

(56) References Cited

U.S. PATENT DOCUMENTS

| | | |
|---|---|---|
| 5,406,950 A | 4/1995 | Brandenburger et al. |
| 5,458,131 A | 10/1995 | Wilk |
| 5,467,100 A | 11/1995 | Chen |
| 5,476,100 A | 12/1995 | Galel |
| 5,562,603 A | 10/1996 | Moll et al. |
| 5,599,294 A | 2/1997 | Edwards et al. |
| 5,611,344 A | 3/1997 | Bernstein et al. |
| 5,704,361 A | 1/1998 | Seward et al. |
| 5,752,938 A | 5/1998 | Flatland et al. |
| 5,775,328 A | 7/1998 | Lowe et al. |
| 5,810,757 A | 9/1998 | Sweezer, Jr. et al. |
| 5,837,221 A | 11/1998 | Bernstein et al. |
| 5,853,698 A | 12/1998 | Straub et al. |
| 5,855,614 A | 1/1999 | Stevens et al. |
| 5,879,324 A | 3/1999 | von Hoffmann |
| 5,924,424 A | 7/1999 | Stevens et al. |
| 5,944,019 A | 8/1999 | Knudson et al. |
| 5,957,849 A | 9/1999 | Munro |
| 6,026,814 A | 2/2000 | LaFontaine et al. |
| 6,030,365 A | 2/2000 | Laufer |
| 6,117,105 A | 9/2000 | Bresnaham et al. |
| 6,193,680 B1 | 2/2001 | Parsons et al. |
| 6,296,654 B1 | 10/2001 | Ward |
| 6,689,062 B1 * | 2/2004 | Mesallum ................ 600/439 |
| 6,740,101 B2 | 5/2004 | Houser et al. |
| 8,070,680 B2 | 12/2011 | Mesallum |
| 2001/0049497 A1 | 12/2001 | Kalloo et al. |
| 2004/0097801 A1 | 5/2004 | Mesallum |
| 2010/0036197 A1 | 2/2010 | Mesallum |

* cited by examiner

METHOD AND APPARATUS FOR PERFORMING TRANSESOPHAGEAL CARDIOVASCULAR PROCEDURES

CROSS-REFERENCE TO RELATED APPLICATIONS

This application is a continuation of and claims the benefit under 35 U.S.C. §120 of U.S. application Ser. No. 13/310,548, filed Dec. 2, 2011, which application is a continuation of U.S. application Ser. No. 11/050,284, filed Feb. 3, 2005, now U.S. Pat. No. 8,070,680, which is a continuation of U.S. application Ser. No. 10/700,113, filed Nov. 3, 2003, now abandoned, which is a continuation of U.S. application Ser. No. 09/718,642, filed Nov. 22, 2000, now U.S. Pat. No. 6,689,062, which claims priority under 35 U.S.C. §119(e) to U.S. Provisional Application Ser. No. 60/167,147, filed Nov. 23, 1999, each of which is herein incorporated by reference in their entirety.

BACKGROUND OF THE INVENTION

1. Field of the Invention

The present invention relates generally to a minimally invasive approach to perform transesophageal cardiovascular and mediastinal procedures. More specifically, the invention relates to implementing the concept of transesophageal access to the heart, great vessels and related structures. The invention describes devices and methods to create a transesophageal access to the heart and surrounding structures to perform a body of surgical procedures within a beating heart and on other surrounding structures.

2. Background of the Invention

The access to the human heart has always been a source of active research especially recently with the advancement in technology that has led to improved management of cardiovascular pathology. Heart disease is the leading cause of death connected to all age groups in the United States. The esophagus has a close proximity to the heart and posterior mediastinum, which has allowed the use of transesophageal fine needle aspiration and transesophageal biopsy techniques to be used extensively in recent years to obtain tissue samples. Most of the posterior mediastinal tissues are accessible for biopsy including the lungs and lymph nodes. The technique has proven to be safe and reproducible with minimal complications. The microbial flora of the human esophagus is similar to that in the pharynx, which results in no bacteremia with transesophageal puncture using needles up to 1 mm in diameter in many studies. The esophagus has never been used to access the human heart, but rather to perform procedures related to the heart due to the close anatomical proximity. A number of trials have been described as in U.S. Pat. No. 6,120,442 for transesophageal intracardiac pressure measurement, in U.S. Pat. No. 5,417,713 for using a transesophageal defibrillating system, and in U.S. Pat. No. 5,179,952 for the use of a transesophageal electrocardial stimulator. Some trials were made to use the trachea for monitoring the heart as in U.S. Pat. No. 5,080,107 that describes the use of an endotracheal sensor for cardiac monitoring.

Access to the heart has always been the main determinant of the form, degree and invasiveness of therapy, which determines the ultimate success of the treatment modality. The left side of the heart is more systemically important and much less accessible than the right side for its anatomic location and the high blood pressure it generates in the systemic circulation. The spectrum of disease states that can be assessed diagnostically or therapeutically are generally more reflected on the left side of the heart. This is evident clinically in a wide range of cardiovascular pathology e.g. congestive heart failure. There is no known non-invasive method that can directly measure the pressure in any chamber of the heart. All current methods either use speed of blood flow as a non-invasive reflection of chamber pressure or they measure the pressure invasively via a catheter inside or near the chamber. The most common technique to measure the left atrial pressure is the pulmonary catheter wedge pressure method. The left atrium is a low-pressure, left-sided structure that has a special importance with regard to its mechanical and electrical properties. Unfortunately, there is no simple non-invasive way of directly measuring the left atrial pressure. Even with invasive measurement as in pulmonary artery catheterization, the measured value reflects an indirect estimation of the left atrial pressure, and thus can be inaccurate in many instances. The left atrium is also important in terms of electrophysiological mapping and ablation. The current techniques access the left atrium using a catheter indirectly from the right atrium across the inter atrial septum or in a retrograde approach through the aorta. Both techniques have their inherent side effects and complications. Thus, access to the left atrium is a described objective in order to treat a large subset of patients, such as congestive heart failure patients.

A second subset of cardiac patients in which the access to the heart is the main determinant of interventions and management are patients with congenital cardiac defects like ASD, VSD and PDA. The main pathology in most congenital cardiac defects is the presence of an unnatural conduit that shunts the blood from the right to left heart or the reverse. This overloads the side with lower pressure and any tissue or vascular bed in the shunted circuit. The pulmonary vascular bed is commonly affected by blood overflow that may lead to reversible or late irreversible pulmonary vascular hypertension. The invasiveness of the current techniques limits the early implementation of a shunt closure especially in children, which is a curative intervention if done before irreversible vascular changes. Other techniques use the catheter transvascular approach with limited success due to lack of control and torque at the end of a long flexible, narrow catheter used in the procedure.

In a third group of patients, cardiac arrhythmias are responsible for a high percentage of morbidity and mortality. Atrial fibrillation is a common and chronic disease with a prevalence of 2-3% in the United States. The disease is longstanding and mandates chronic anticoagulation as part of the treatment to prevent any embolic disease especially to the brain. Chronic anticoagulation in itself carries serious risk of internal bleeding added to the toxicity of chronic anti-arrhythmic medications used to stabilize atrial fibrillation. Recently, surgical curative techniques have been described in the literature to treat atrial fibrillation. Access to the heart has been a main determinant in the use of any of these techniques. The invasiveness of the open chest approach has limited the number of the Maze-like procedures used to radically prevent the fibrillation impulses from being conducted to the ventricles. Also, the catheter-based approach is inaccurate, tedious, time consuming (up to 12 hours) and not definitive in creating enough linear ablations to prevent impulse conduction. The thoracoscopic approach is easier than the catheter-based transvascular approach but the side access to the posterior heart limits the linearity of ablation especially around the entrance of the pulmonary veins, which results in incomplete Maze, and recurrence of disease.

The three known accesses to the heart namely, the open chest, the catheter-based transvascular, and the thoracoscopic approaches suffer from serious limitations and complications which, in turn, limit the therapeutic options for most of patients. The limitations of the current three known accesses to the human heart can be classified as follows:

1—The Open-Chest Technique:

Most cardiovascular procedures are performed by opening the chest wall either by gross sternotomy or by lateral thoracotomy. The sternotomy approach is more common than the lateral thoracotomy as it allows a greater field for the surgeon to introduce surgical devices, to control target tissues and to clamp and catheterize the aorta for induction of cardioplegia and bypass. It involves opening the sternum using a saw to cut through the bony structure. It also involves arresting the heart by cardioplegic techniques. The circulation is switched to cardiopulmonary bypass for preserving tissue perfusion. The above advantages of the sternotomy approach are offset by serious disadvantages. First, the risk of stopping the circulation with the possibility of causing marked decrease in tissue perfusion or ischemic damage that may involve vital tissues like the brain, heart or kidneys. Second, the risk of embolization of dislodged tissues in the aorta due to aortic manipulation including clamping and catheterization. The dislodged emboli can cause acute brain or peripheral ischemia. Brain damage may be permanent after an embolic event during open sternotomy approach. Even without any embolic or gross brain injury, psychometric analysis shows definite changes and cognitive defects in young healthy individuals after open-heart surgery. Third, opening the chest wall by cutting through all layers including the bony sternum with great force applied for rib retraction produces significant pain after the surgery with post surgical morbidity and, if severe, mortality. The post surgical wound care and pain may require rehabilitation in complicated cases with longer hospital stays and increased expenses. Fourth, concomitant morbid states or age extremes may adversely increase all of the above-mentioned risks.

The other two methods to access the heart are the transvascular and the thoracoscopic approaches. Both have the advantageous difference from the conventional open-chest approach in not requiring gross thoracotomy. The thoracoscopic approach may or may not involve cardioplegia and cardiopulmonary bypass. Again, these procedures have fundamental disadvantages.

2—The Transvascular Approach:

For the transvascular approach to the treatment of heat defects, the disadvantages are inherent in the fact that the procedural tools have to go through and stay in a blood vessel or a cardiac chamber. Thus, the tools can only be long, narrow, flexible catheters. This affects the controllability and the force generation at the tip of the catheter which, in turn, decreases the accuracy and precision of the procedure. The access to the heart is mainly from the right side and rarely through an aortic retrograde approach. To reach the left heart, a septostomy opening is made in the interatrial septum that decreases the control over the catheter and makes the manipulation of the catheter tip more difficult as the catheter has to pass through the narrow right atrium and the small septostomy opening. Another main limitation is the caliber of the lumen of peripheral vessels through which the catheter has to travel. This is even a more limiting factor in young children whose smaller vessels raise the risk of vessel injury that may be acute, such as intimal dissection, or chronic such as major vascular obliteration and fibrosis. In the elder population, the occurrence of peripheral fat embolization is another risk for manipulations of a catheter in the aortic lumen for procedures like coronary angiography. This may result in temporary acute or chronic ischemia to the lower or upper extremities.

In addition to vascular injury, some techniques like intracardiac mapping and ablation require the passage of large catheters to be able to deliver large energy output through large electrodes. These ablative techniques are useful in cardiac dysrrhythmias as ventricular or supraventricular tachcardias and atrial fibrillation. A number of trials to apply mapping and ablation technique through the use of the transvascular approach have been described as in U.S. Pat. Nos. 4,960,134, 4,573,473, 4,628,937, and 5,327,889. In U.S. Pat. No. 6,047,218, a technique for ablation and visualization of the intracardiac chamber through the transvascular approach is described. The small size of the vessels limits the size of catheters used in ablation techniques. That limitation gives rise to a lack of control and positionability due to the flexibility, increased distance and decreased force at the tip of such catheters.

The transvascular approach has a limited use in surgical procedures like septa defect repair by using an introductory device due to the above-mentioned limitations. A number of trials to use the transvascular approach to deliver a patch from a vein via the right heart to close a septal defect have been contemplated; see e.g. U.S. Pat. Nos. 3,874,388; 5,334,217; 5,284,488; 4,917,089, and 4,007,743. In addition to the above-mentioned limitations, the use of patches to close a septal defect using the transvascular approach with lack of distal force at the delivery tip may result in inadequate fixation of the patch to the defect plus the inability of patch repositioning after its application to the defect site. The detachment of the patch from the defect site may lead to serious patch embolization and failure of repair. In some cases this may, in turn, require an open sternotomy to correct the failed transvascular repair.

3—The Thoracoscopic Approach:

The thoracoscopic approach provides more advantages over the transvascular approach in terms of having more control over the procedure tools, and increased precision in positioning the catheter tip to perform intracardiac procedures. The disadvantages of such an approach can be considered. The inaccessibility of the posterior aspect of the heart to the rigid scopes passed from either side of the heart, which is mandatory to create an atriostomy opening in the posterior aspect of the atrium, is a problem. This may be solved by applying a stitch to the pericardium and pulling the pericardium to rotate the heart and expose the posterior aspect. The stitch should be applied from an anterior, not side, position to have enough rotation force on the pericardium. However, due to the narrow intercostals spaces in the anterior rib aspect, it is difficult to make such a stitch which makes the posterior aspect of the heart a difficult area to access. Another limitation is the need to have a second monitoring system to assess catheter position and convey accurate measurements as the procedure is not performed under direct visual examination. Such monitoring devices make the approach more complicated, may lack accurate precision, and may need to be invasive, e.g. removal of the fourth rib for visualization, or add a potential risk of ionizing radiation exposure with CT scanning, or be cumbersome and slow with MRI scanning, adding to the complexity of the technique. Second, the limited windows between the ribs as a limiting border from above and below the access, the surrounding intercostals muscles and underlying vital structures including the lungs, pleura, nerves, and great vessels can limit the access specially in young children with narrow intercostals spaces, and patients with deformities.

The need to access multiple intercostal openings to use a plurality of thoracoscopes counteracts the main objective of the technique to be minimally invasive and may turn out to be more invasive and cause significant tissue damage as it may also require removal of the fourth rib. The need to deflate the lung to widen the surgical field adds to the invasiveness and increases the complication potential of the procedure. The inability to explore the posterior mediastinum and related structures on the posterior aspect of the heart as the catheter is advanced from an anterior position makes procedures involving the posterior aspect of the heart less accessible as in ablation around the entrance of the four pulmonary veins in the left atrium. Indeed, the thoracoscopic approach has been criticized lately by a number of studies that show numerous post-surgical complications. A number of trials to perform surgical intracardiac procedures from the thoracoscopic approach have been described, e.g. in U.S. Pat. Nos. 5,980,455; 5,924,424; 5,855,614; 5,829,447; 5,823,956; 5,814,097; 5,797,960; 5,728,151; 5,718,725; 5,713,951; 5,613,937, and 5,571,215. Closed chest coronary bypass surgery using the thoracoscopic approach is described in U.S. Pat. No. 6,123,682.

None of the currently available techniques directly accesses the posterior aspect of the heart and coronary circulation or the posterior mediastinum. Recently, there has been heightened interest in minimally invasive methods of cardiac surgery that allow intracardiac or extracardiac procedures and avoid the need to crack the rib cage or stop the heart.

What are needed, therefore, are devices and methods to enable a new access to the human heart that is easily accessible, that allows access to both the interior and exterior of the heart simultaneously, with enough force and control over the procedure tools, that causes minimum tissue injury, and that can be applied to the heart, while still beating, without the need for general anesthesia. This access should allow the performance of surgical procedures like septal defect repairs, treatment of cardiac dysrrhythmias and treatment of various cardiac pathology such as valvular manipulations with a degree of success similar to the open approaches, while avoiding the complications and limitations of the above-mentioned prior techniques.

SUMMARY OF THE INVENTION

Accordingly, it is a principal object of the invention to provide method and means for providing a transesophageal access to the heart, great vessels, posterior mediastinum and all related structures.

The invention provides procedures that can safely and accurately create a transesophageal access into the heart, pericardium, posterior mediastinum, the great vessels and all related structures. The procedures can be carried out on a beating heart without the need for stopping the heart, cardiopulmonary bypass or gross or minor thoracotomy. This transesophageal access can be used to perform a variety of diagnostic and therapeutic procedures including but not limited to:

(1) Esophageal: manipulations, insertion of intra or extraesophageal devices to sense and control the electrical and mechanical properties of the esophagus and stomach; transesophageal electrical cardiac pacing, mapping and ablation; dual combined stereoscopic 3D ultrasound imaging of the heart from the transesophageal and intracardiac positions;

(2) Posterior mediastinum: insertion of mediastinal devices for chronic sensing and control of electrical, chemical, mechanical, genetical, pharmacological, and physical manipulation of tissues in the posterior mediastinum and related structures such as lymph nodes, lungs, nerves, vessels, heart, esophagus, diaphragm and stomach; posterior mediastinal electrical cardiac pacing, mapping and ablation;

(3) Pericardium: accessing the pericardial space for assessment and control of intrapericardial electric, mechanical, physical, genetical, pharmacological and chemical properties, aspiration and biopsy of the pericardium or pericardial effusions, excision of the pericardium, pericardiotomy, or pericardial tumor removal; epicardial ultrasound; pericardial assessment of intracardiac chamber pressure, insertion of a sensor to chronically perform a variety of functions as will be mentioned in detail in one of the preferred embodiments of the invention; insertion of intrapericardial catheters for electrical, chemical, mechanical, genetical, or pharmacological interventions; extracardiac transmyocardial laser revascularization; extracardiac electrophysiological mapping and ablation; extrapericardial myocardial assist device insertion and manipulations;

(4) Intracardiac: intracardiac imaging including intracardiac endoscopy, intracardiac ultrasound; repair of valvular diseases such as mitral valvotomy, excision or laser evaporation of vegetations, laser vavuloplasty of the mitral, tricuspid or the aortic valves; laser transmyocardial revascularization; electrophysiological mapping and ablation for treatment of most arrhythmias including atrial fibrillation; repair of congenital abnormalities as ASD, VSD, PDA; anterograde, retrograde, transmyocardial or transepicardial coronary manipulations, revascularization, and bypass of intraluminal obstruction; septal myotomy; endomyocardial biopsy; insertion of intracardiac transient or permanent assist devices; and various other intracardiac procedures that can be performed transesophageally while the heart is beating;

(5) Great Vessels: pulmonary thrombectomy and revascularization, repair of congenital abnormalities such as PDA and transposition of great vessels; sensing and manipulation of venacaval, aortic, pulmonary arterial and pulmonary venous pressures; insertion of transient or permanent intravascular diagnostic and therapeutic devices such as catheters, sensors, drug-delivery vehicles, imaging probes, stents, balloons and the like.

In a first aspect of the invention, a tubular intraesophageal device, to with: an access main unit (AMU) is provided for accessing the lumen of the esophagus, disinfecting the surface mucosa through special porous channels, isolating a long segment in the esophagus behind the heart, blocking any secretions from above or below the segment by inflating an elongated balloon, maintaining sterilization of the isolated segment by establishing a continuous suction-irrigation circulation between the outside surface of the AMU and the esophageal mucosa. The AMU includes an elongated flexible tubular body configured to extend through the esophagus from the pharynx to a predetermined distance below the middle third of the esophagus and above the gastro-esophageal junction. The AMU has an open area on its outside surface, denominated the access exit field (AEF), to allow for creation of the access through the esophageal wall. The AMU contains a plurality of elongated tubular lumens of specific dimensions to allow for the passage of various elongated flexible devices or tools to be described. These lumens include the intraesophageal longitudinal lumen (ILL) that is a collapsible, double layered, wide lumen, open from both ends, and extends from the proximal end to beyond the distal end of the AMU. The ILL can carry an ultrasound probe for procedure monitoring and creation of a 3D stereoscopic ultrasound image of the heart and surrounding structures after the addition of the intracardiac image from an intracardiac ultrasound probe as mentioned below.

A second lumen of the AMU is the transesophageal access lumen (TAL) which is a longitudinal lumen that extends from the proximal end of the AMU and travels along its length to make a 90.degree. angle at its lower end and exits perpendicular to the main axis of the AMU in the center of the AEF. The TAL carries elongated flexible devices including an access side unit (ASU) that penetrates through the esophageal wall and creates an access to the desired target area outside the esophagus. A third tubular lumen inside the AMU is the suction lumen (SL) used to create a negative pressure in the space of the AEF between the outer surface of the AMU and the esophageal mucosa. The SL also allows for suctioning of any secretions that may escape into the AEF.

According to the invention, the ASU which passes through the TAL is made of two concentric, slidable, small flexible tubes open at both ends. The outer tube is a sheath-like tube that contains small parallel longitudinal tubules along the thickness of the sheath. The tubules are open at their proximal ends. At the distal end, each tubule has a flap that is level with and below the outer surface of the sheath. Each tubule carries a flexible distal-hooked needle extending from the proximal end of the tubule and curving laterally inside the flap at the distal end thereof. The proximal ends of the needles are geared to a dial at the proximal end of the ASU so that the needles can be rotated to move the flaps between retracted and radially extended positions.

The inner tube of the ASU has two separate longitudinal lumens. A smaller lumen carries an endoscope for direct visualization and monitoring of the procedure. A larger lumen may carry various elongated flexible devices to be described for performing selected extra and intra-cardiac procedures. The tip of the ASU has an umbrella with a plurality of supporting flexible, resilient, radially arranged wires and a suitable material extending between the wires to seal the penetration in the esophageal lumen. Each wire carries a knob that can receive and irreversibly attach to the distally hooked needle and the knobs are attached to the ends of suture threads. The threads are coiled on the inner surface of the umbrella and each thread is attached at both ends to two adjacent knobs. This allows the creation of a purse string suture around the distal end of the ASU after penetration through the esophageal lumen by penetration means to be described. The smaller and larger tubes of the ASU are beveled at their distal ends so that the penetration means is tapered along the beveling at both ends. The penetration means can be retracted into the inner lumen of the ASU after they are advanced through the esophageal wall.

As just stated, the ASU may include penetration means within its inner lumen to penetrate through the esophageal wall. The penetration device may be a needle with over-lying dilator, surgical blade, electrosurgical blade, laser blade or any other conventional penetration means. Preferably, the penetration means is beveled in line with the smaller lumen of the inner ASU tube.

The apparatus also includes a transesophageal intracardiac access (TIA) which is similar in structure to the ASU but smaller in diameter to fit inside the larger lumen of the ASU. It can create an opening of 6 mm or more in a cardiac chamber. The TIA allows the passage of elongated flexible devices to the interior of the heart to perform various procedures. In a preferred embodiment, the TIA uses an umbrella at its distal end to seal the penetration through the cardiac chamber wall and to make a purse string suture that is used at the end of the procedure to secure the penetration site. In another embodiment, the sealing means at the distal end of the TIA can be an inflatable balloon, double balloons, or an expandable flange. The short length and wide diameter of the TIA allow for the precise positionability and control of the intracardiac devices.

The TIA may also include a penetration device within its inner lumen to penetrate through the muscular wall of a cardiac chamber. The penetration device may be a needle with overlying dilator, surgical blade, electrosurgical blade, laser blade or any other penetration means. The penetration means can be retracted into the inner lumen of the TIA after it is advanced through the muscular cardiac wall.

The TIA may also include a valve for hemostasis in the inner lumen to prevent blood back flow inside the lumen of the TIA after opening a penetration to the interior of the heart. The valve may be located at the proximal end of the TIA or more preferably at the distal end thereof. The TIA can then be flushed across the hemostatic valve with normal saline to create a blood-saline interface to avoid air bubbles in the lumen of the TIA. If the TIA is positioned in a low pressure chamber like the right or left atrium, the back-pressure of the blood my be low enough to obviate the need for a valve mechanism in the blood-saline interface. After the placement of the TIA inside a cardiac chamber, preferably the left atrium, a wide, short and almost straight access is created from outside the body across the esophagus into the left atrium that allows various devices to be described to perform diagnostic and therapeutic procedures.

Using the TIA mentioned above and in a preferred embodiment, the invention provides devices and methods to repair atrial or ventricular septal defects. The method of repair may include direct purse string closure of a septal defect using an elongated flexible device introduced through the lumen of the TIA and positioned at the septal defect with the aid of either direct endoscopic visualization, intracardiac ultrasound imaging, or combined transesophageal and intracardiac ultrasound stereoscopic imaging as described below. Advantageously, the purse string flexible closure device fixes its working tip to the outer edge of the defect after passing through it by means of a retractable umbrella at said tip. This is a unique way of closure as it uses semi-continuous purse string suturing on a flexible and controllable device. The frame of the umbrella may hold a non-thrombogenic material between its collapsible wires, like polyester or polytetrafluoroethylene film, to temporarily close the defect and record the hemodynamics of the heart to predict the burden of pressure changes inside the heart. The wires of the umbrella are radially arranged and made of a flexible but resilient material such as the material trademark Nitinol™, to be able to pass through the TIA and deploy on the distal aspect of the defect.

The suturing device is similar to the TIA in structure but need not have the wires of the distal umbrella covered with a patch as it is optional to test the hemodynamic effect of the defect closure as mentioned above. The flexible purse string-suturing device (FPSS) is made of two sliding flexible tubes sharing the same longitudinal and transverse axis and sliding on one another. The outer tube of the FPSS constitutes a sheath formed with longitudinal tubules with distal flaps and containing distally curved needles just as in the ASU described above. The proximal ends of the needles carry spur gears which mesh with a ring gear in a dial extending around the proximal end of the FPSS. The distal end of each tubule leads to a groove on the corresponding flap. As with the ASU, the flaps are level with the wall of the sheath when in their normal or horizontal position. By turning the dial, the needles may be rotated so that their turned distal ends move flaps to their radially extended positions.

The inner tube of the FPSS is an elongated flexible tube with proximal and distal ends and a central lumen. It slides tightly inside the outer sheath on the same transverse axis and has a longitudinal groove(s) on its outside surface that slidably receives a matching protuberance(s) extending from the inner surface of the outlying sheath. At its distal end, the inner tube of the FPSS has an array of wires arranged around the distal opening of the tube in an umbrella-like fashion. These wires are collapsible, flexible, and resilient. Each wire moves around an elbow on its connection with the rim of the distal end of the tube. A deploying mechanism such as a spring, coil or similar means connected to the distal end of the tube and the proximal end of each wire, works to deploy and thereby extend the wire perpendicular to the longitudinal axis of the inner tube of the FPSS. The wires are coupled to a set of controlling threads connected to their inner aspect immediately above the elbow connection with the tube. The controlling threads run in grooves in the thickness of the inner tube. By exerting tension on the controlling threads, the wires may be retracted against the deploying mechanism to their original non-deployed flat positions. Advantageously, this technique allows the wires to be re-retracted and re-deploying for appropriate positioning. In the non-deployed state, the wires are parallel to each other and to the long axis of the tube and lay level with the surface of the inner tube. Upon deployment, the wires fan out and are generally perpendicular to the tube.

Each wire carries a knob on its inner aspect. The knob is a hollow structure that captures the tip of a hooked needle. This fitting forms a one-way coupling by virtue of the shape of the undermined lumen. Each knob is connected to one end of a thread, while each two adjacent knobs are connected by one thread. Thus, if the FPSS has 8 wires at its distal end, and each wire carries a knob, this means that there are 4 continuous threads carried by the 8 knobs.

In one procedure according to the invention, the FPSS is passed towards a septal defect. The distal end of the device is passed into the heart chamber on the side of the cardiac septum distal to the point of introduction, e.g., the right atrium if the device has been introduced through the left atrium across the defect and the wires are deployed to a perpendicular position on the distal end by means of a deploying mechanism that can be reversed later. The wires may be spread out radially by decreasing the tension on the controlling threads, and releasing the deploying mechanism.

The FPSS may be pulled back slightly so that the wires are flat with the outer surface of the septum while the lumen of the device is inside the defect. The wires are now on one side of the defect while the sheath or outer tube is on the other side. By turning the aforesaid dial on the FPSS 90.degree., the flaps may be moved to extended positions perpendicular to the sheath. The needles are pushed down in the grooves by means of a plunger or similar device. The outward groove in each flap directs the needle in that flap to extend in a fixed direction. That needle penetrates the septum around the defect at a predetermined distance away from the center of the device that allows the needle's hooked tip to reach inside the undermined lumen of the knob carried on each wire on the other side of the septum.

The needles are thus tightly coupled to the knobs on the wires and hence to the thread attached to the knobs. The needles may be withdrawn back across the septum into the corresponding flaps of the outer sheath. The dial on the outer sheath may then be rotated back return the flap to their original retracted or horizontal positions and the whole sheath with its needles may be withdrawn outside the body. The threads are long enough to come out from around the septal defect, coupled to the tips of the needles. The threads may then be cut just below the connection with the needles leaving the physician with either 4 or 8 thread ends depending on the kind of FPSS used.

In a preferred embodiment of the invention, a device to tie the threads together comprises a thin sheet of Vicryl or similar absorbable material, to connect two ends of the threads together by compressing the sheet of Vicryl to form a tight cylinder around both ends. Knotting, gluing, or similar means can also accomplish the tying. By connecting the ends of consecutive threads together, a continuous loop of thread is formed in the shape of a purse string suture loop. The inner tube of the FPSS is pushed slightly into the defect to allow the controlling threads to retract the umbrella wires to the original flat non-deployed state. After retraction of the wires, the inner tube of the FPSS is withdrawn from the defect through the TIA to outside the patient's body. By pulling the two terminal ends of the purse string suture loop, the suture tightens and the defect is closed. The two ends are then tied together to form a knot, and the knot is pushed down by a flexible elongated knot-pusher that may be pushed down the lumen of the TIA.

The same technique described above can be used to close the esophageal and cardiac penetration sites formed by the ASU and TIA, respectively. This suturing technique is described for exemplary purpose only. The method of the invention can be used for any catheter-based purse string suturing intervention.

The lumen of the FPSS may also carry an imaging element for accurate positioning, monitoring and validation of the closure of the defect. This imaging element can be an endoscope with a balloon on the distal end to allow visualization through blood or with a CCD chip to create an image reflected through blood as described in the prior art. The imaging element can preferably be an ultrasound probe that is either used alone or in combination with the transesophageal probe in a synchronized fashion to create a 3D, stereoscopic ultrasound image. The synchronization can be accomplished in one of two ways. The first is to use two probes with two separate energy sources. Each probe acquires images separately and also acquires information about its own position with regard to the heart from the other probe. The probes alternate with high frequency to produce signals to avoid noise and distortion. The second method is having the signal produced by one probe received by the other probe in a continuous fashion. In this case, both probes can split one energy source and one receiver. The signals representing the images from both probes are fed to a multiplexer for image registration and then to a microprocessor for reconstruction. This allows for the creation of a 3D image of the area examined by moving the probes from two different orientations. The image can be displayed on line or stored for later processing. The technique of creating 3D ultrasound images can be achieved using the transesophageal probe alone by having two ultrasound transmitter/receivers spaced apart by a changeable distance so that the signal produced by one transmitter is received by the distant receiver and vice versa. By positioning one transmitter receiver in a distal position such as in the stomach and the other in a proximal position such as in the esophagus, a combined stereoscopic ultrasound image can be created. The stomach transmitter/receiver unit can be tilted and moved away or towards the esophageal unit to create a more detailed image of the heart from various locations.

BRIEF DESCRIPTION OF THE DRAWINGS

The invention will be clarified by the following description taken in connection with the accompanying drawings, in which.

DESCRIPTION OF THE PREFERRED EMBODIMENTS

Figure 1:
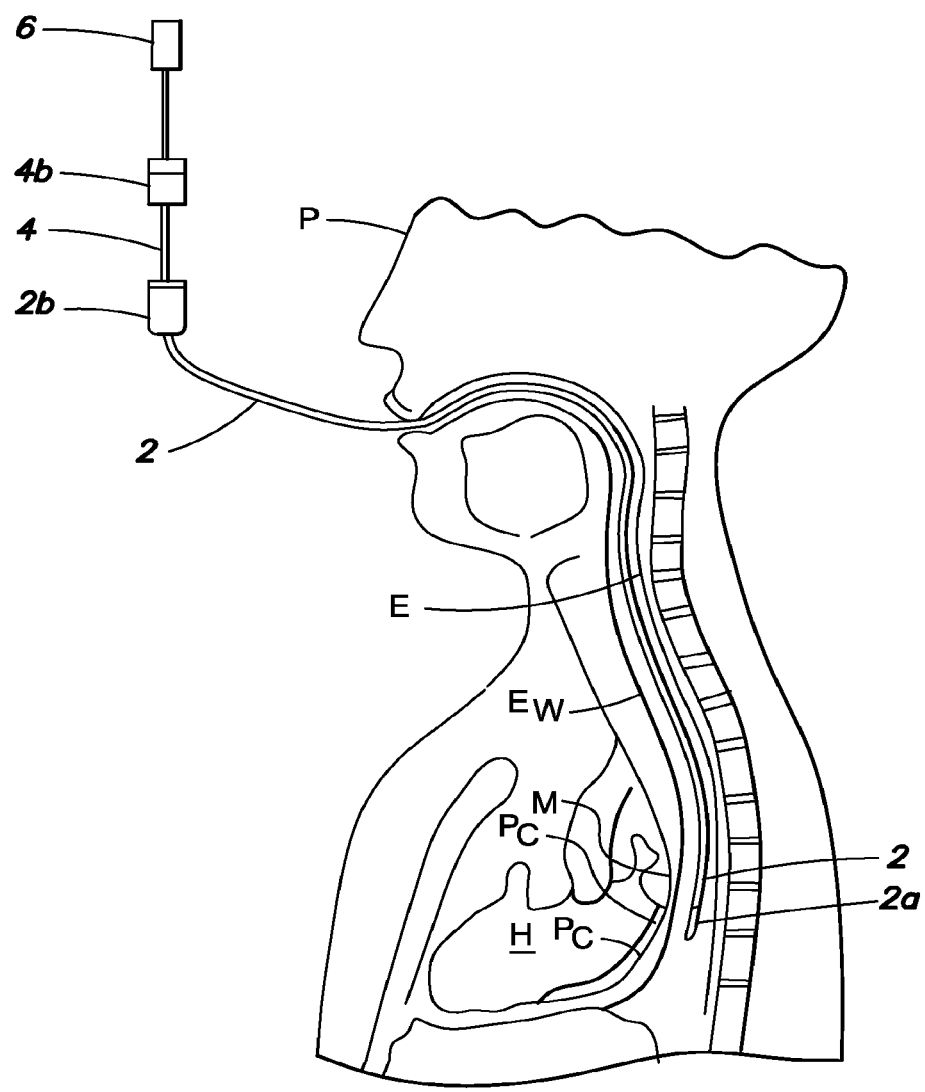
FIG. 1 is a diagrammatic view showing apparatus according to the invention introduced into a human torso.

Referring to FIG. 1 of the drawings, my apparatus comprises an access main unit (AMU) 2 which may be inserted via the month into the esophagus E of a patient P so that the distal or working end 2a of AMU 2 is located behind the patient's heart H. The apparatus also includes an access side until (ASU) 4 which is received in AMU 2 and whose distal end protrudes from AMU end 2a and is designed to penetrate the esophageal wall E.sub.w to access extraesophageal regions in the patient's body such as the posterior mediastinum M. Another component of the apparatus is a transesophageal intercardiac access device (TIA) 6 which is received in ASU 4 and whose distal end may protrude from the ASU so that it may penetrate the pericardium PC and access heart H.

1) The Access Main Unit (AMU) 2

Figure 2A:
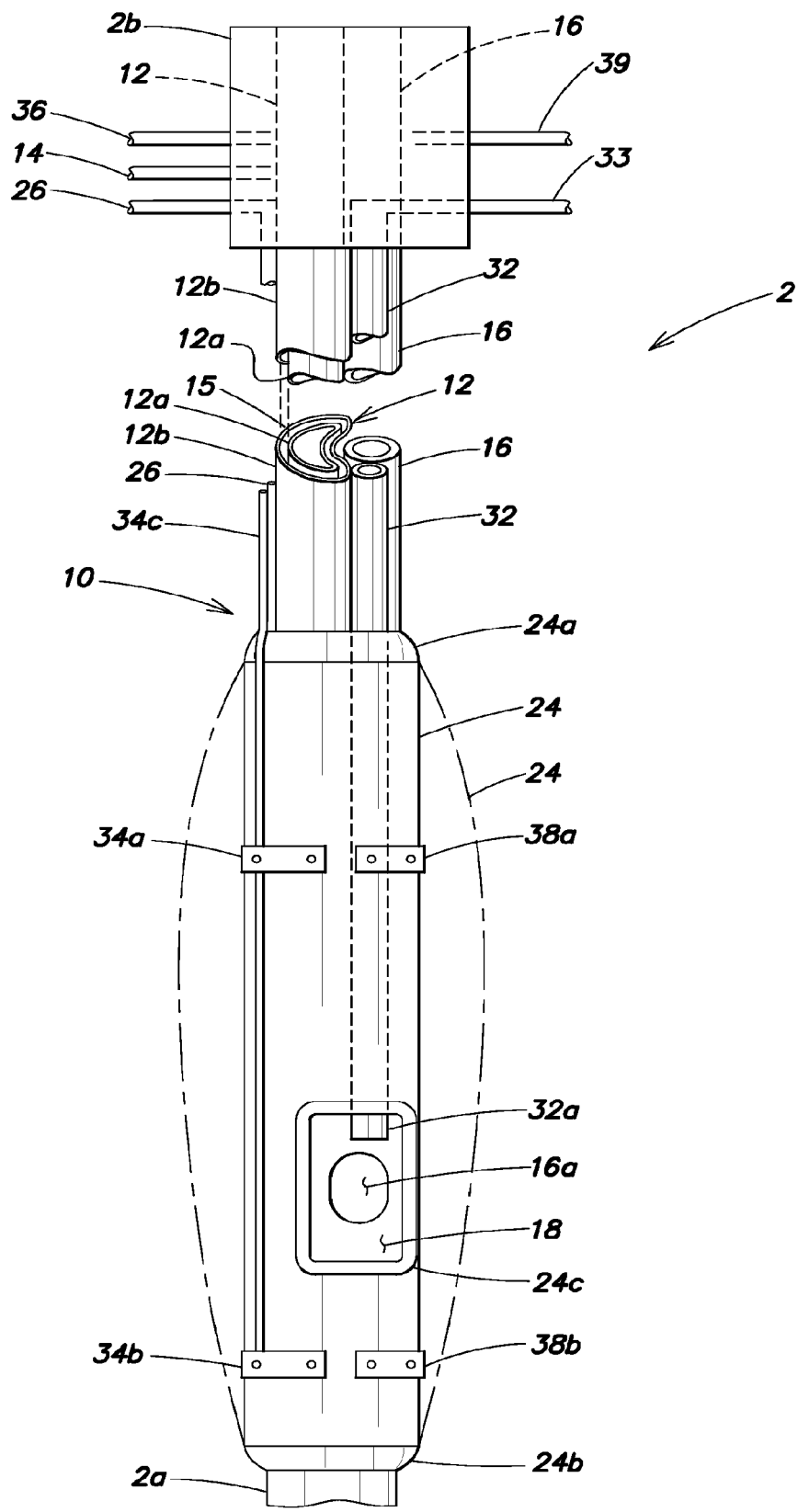
FIG. 2A is a front elevational view on a much larger scale and with parts broken away showing the AMU component of the FIG. 1 apparatus in greater detail.
Figure 2B:
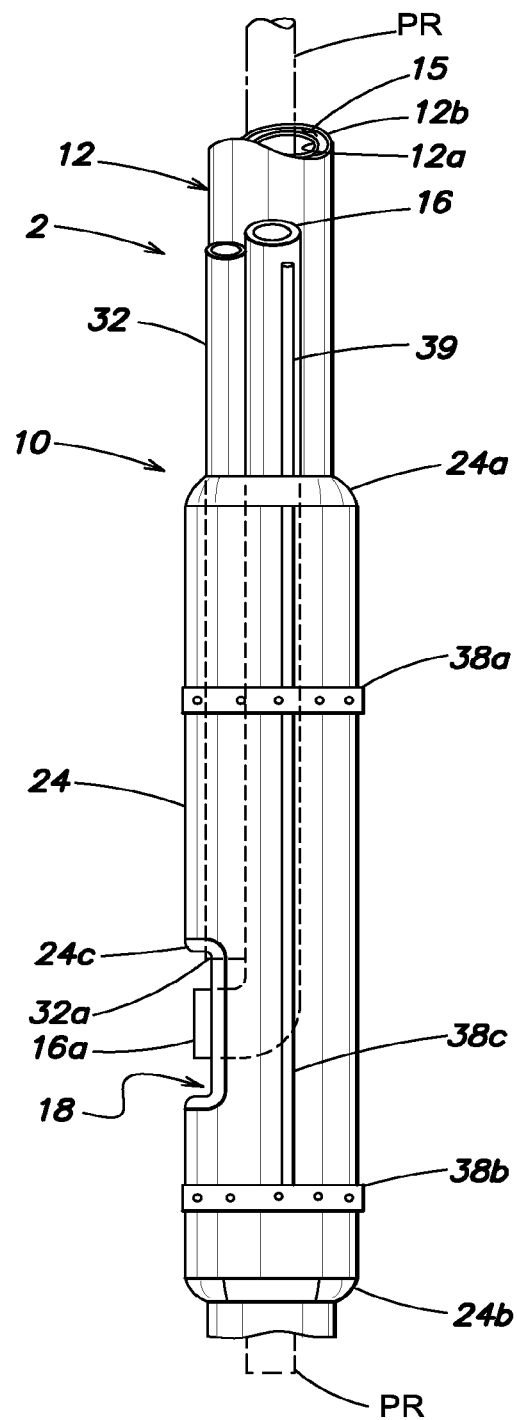
FIG. 2B is a side elevational view thereof.

Referring to FIGS. 1, 2A and 2B of the drawings, AMU 2 may be inserted into the lumen of the esophagus E so as to isolate a segment of the esophagus behind the heart H. AMU 2 comprises an elongated flexible catheter 10 having a plurality, preferably at least three, lumens. The lumens include an intraesophageal longitudinal lumen (ILL) 12 open at both ends that is a double wall structure composed of a collapsible inner wall 12a and an outer wall 12b. A conduit 14 at the proximal end 2b of the AMU extends into the space 15 between walls 12a and 12b. When that conduit is connected to a source (not shown) of fluid under pressure, the inner wall 12a may be pressed against a more or less conventional probe PR, e.g. an ultrasonic probe, present in lumen 12 as shown in phantom in FIG. 2B. This prevents fluids from travelling along the space between the probe and the wall 12a.

AMU 2 also includes a transesophageal access lumen (TAL) 16 which extends from the proximal end 2b of the AMU to a location spaced from the distal end 2a thereof where it makes a 90.degree. turn so that its distal end forms an opening 16a in the side of the AMU. The area around the opening is denominated the access exit field (AEF) 18 of the AMU. TAL 16 is dimensioned to accommodate ASU 4 (FIG. 1) which is an elongated flexible probe-like device to be described for penetrating the esophageal wall and creating an access to a selected target area outside the esophagus.

Still referring to FIGS. 2A and 2B, the distal end segment of AMU 10 carries an elongated balloon 24 which extends above and below AEF 18, i.e. between boundary seals 24a and 24b. The balloon also has a third boundary seal 24c which encircles AEF 18. Balloon 24 may be inflated by introducing a fluid under pressure into a conduit 26 (FIG. 2A) extending from the proximal end 2b of AMU 2 into the balloon. When the AMU 2 is present in the esophagus and balloon 24 is inflated as shown in phantom in FIG. 2A, the balloon 24 presses against the esophageal wall except at AEU 18 which thus creates an isolated area within the esophagus between the AMU and the esophageal mucosa.

The inflated balloon also enhances the ultrasound transmission/reception of the ultrasound probe PR that may be present in TAL 16.

Preferably AMU 10 also includes a suction lumen (SL) 32 whose distal end 32a extends to AEF 18. The proximal end of SL 32 may be connected via a conduit 33 to a vacuum source (not shown) to suck away any secretions that may leak into AEF 18 when balloon 24 is inflated.

Preferably also provision is made in AMU 2 for establishing a continuous circulation of a sterile fluid between the AMU and the esophageal mucosa in the region surrounding AEF 18. More particularly, arcuate upper and lower perforate channels 34a and 34b are formed in the walls of the balloon 24 at one side of the AMU above and below the balloon boundary seal 24c that defines AEF 18. These channels are interconnected by a longitudinal channel 34c and connected via a conduit 36 to a source of sterile irrigation fluid, e.g. saline and/or disinfectant. Also present in the balloon wall at the other side of the AMU is a similar pair of upper and lower perforate channels 38a and 38b interconnected by a longitudinal channel 38c. These channels are connected by a conduit 39 to a vacuum source (not shown). Thus, the AMU may establish a continuous suction irrigation circulation via the holes in the channels 34, 38 between the outside surface of the AMU and the wall of the esophagus above and below AEF 18. The continuous suction also causes the inflated AMU balloon 24 to be close to the esophageal wall and helps to remove secretions before they can reach AEF 18.

2) The Access Side Unit (ASU) 4

Figure 3A:
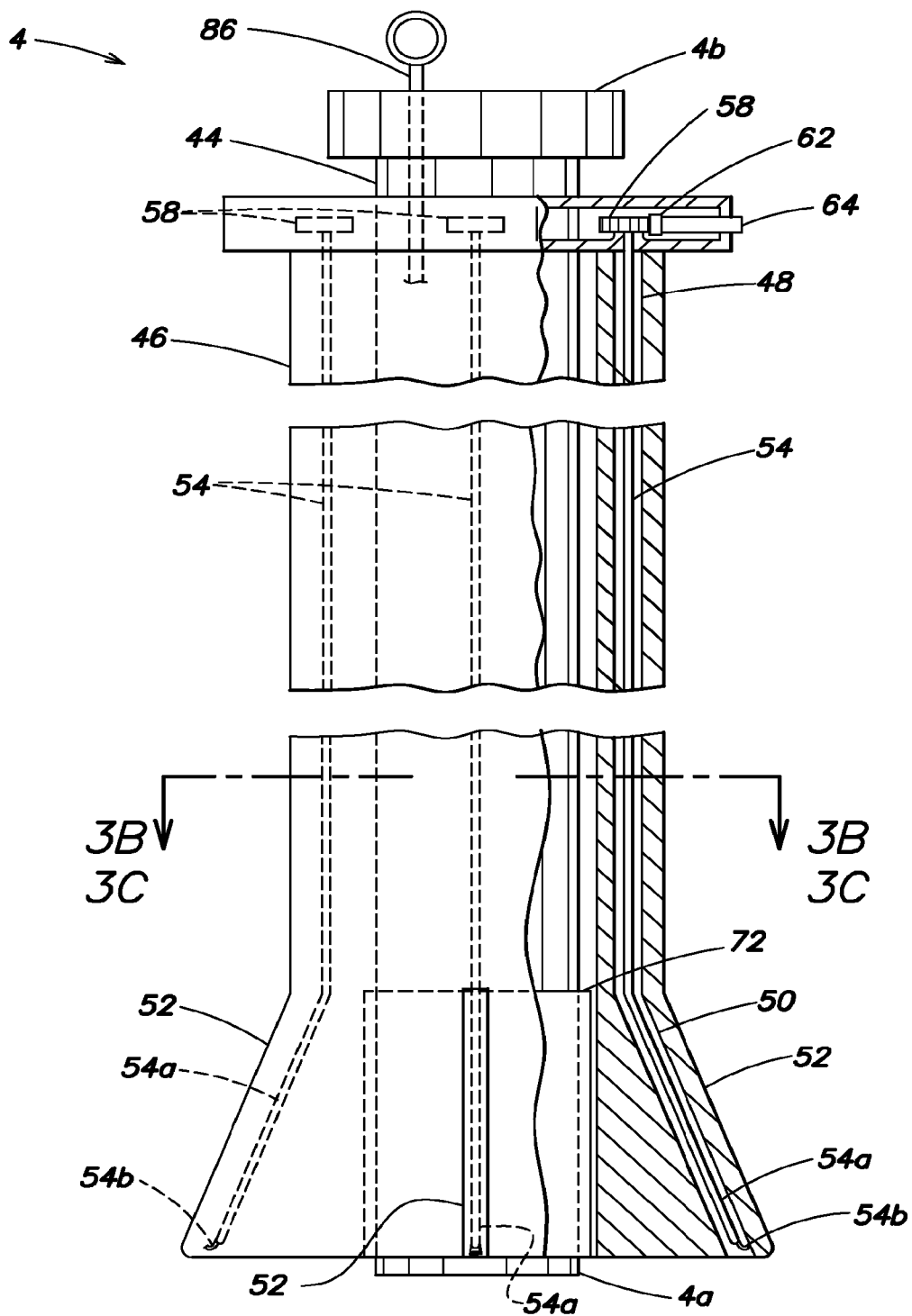
FIG. 3A is an elevational view with parts broken away showing the ASU component of the FIG. 1 apparatus in its flaps-extended condition.
Figure 3B:
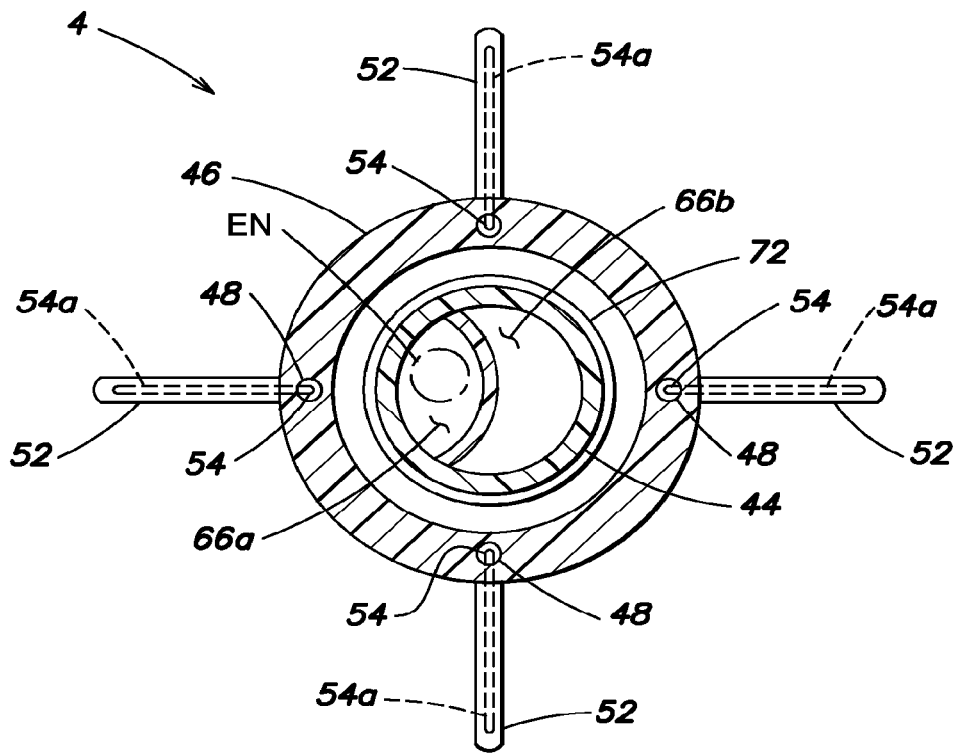
FIG. 3B is a sectional view taken along line 3B-3B of FIG. 3A.

Refer now to FIGS. 3A and 3B which illustrate a second component of my apparatus, to with: the access side unit (ASU) 4. ASU 4 is configured to extend transesophageally inside the TAL 16 of AMU 2 such that its distal end 4a exits the end opening 16a (FIG. 2B) of the TAL and extends across or through the wall E.sub.w (FIG. 4C) of esophagus E to a position outside the esophagus, e.g. the posterior mediastinum M (FIG. 1), the proximal end 4b of ASU 4 being located outside the patient's mouth as shown in FIG. 1. In an exemplary embodiment, the ASU 4 may be 30-40 cm long and have an OD of 5-10 mm. It should be of a flexible material such as a low durometer polymer or silicone.

ASU 4 comprises an inner tube 44 and a concentric outer tube 46, both tubes being open at both ends and slidable relatively. The outer tube 46 has a relatively thick wall formed with a plurality, e.g. four, of longitudinal passages 48 leading to grooves or passages 50 in four distal end flaps 52 on tube 46 which flaps may be flexed from retracted positions wherein the flaps lie against or level with the remainder of outer tube 46 (FIG. 3C) and extended positions wherein the flaps 52 extend out radially from tube 46 (FIG. 3B).

Slidably received in passages 48, 50 are long flexible needles 54 having curved or bent distal end segments 54a which extend along grooves 50 in flaps 52. The proximal ends of needles 54 carry small gears 58 which mesh with a ring gear 62 formed on the inside surface of a dial 64 rotably mounted to the proximal end of ASU 4. The distal ends of the needles have hooks 54b. When the dial 64 is rotated in one direction, the individual needles 54 are rotated about their axes so that their curved end segments 54a extend out from the ASU thereby flexing the flaps 52 to their extended positions shown in FIGS. 3A and 3B. Turning the dial in the opposite direction rotates the needles so that their end segments 54a lie against outer tube 46 so that flaps 52 are retracted against, or more preferably, are flush with the exterior surface of tube 46 as shown in FIG. 3C.

Figure 3C:
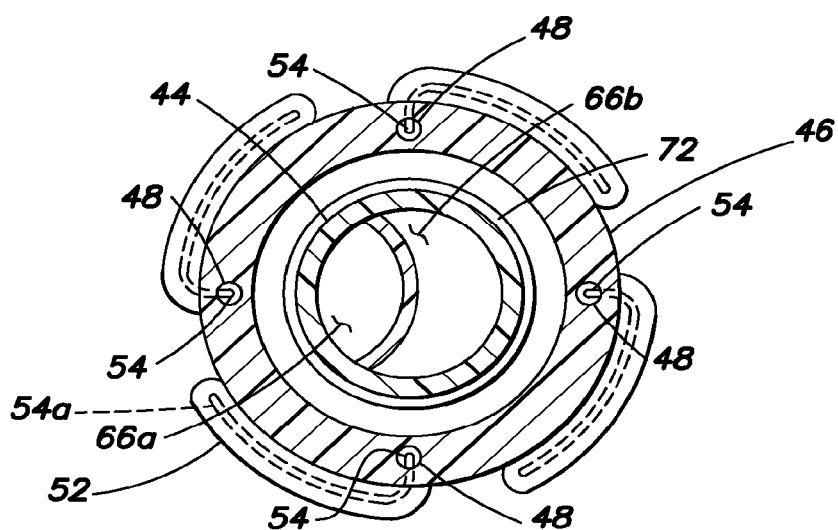
FIG. 3C is a similar sectional view showing the ASU in its flaps-retracted condition.

As shown in FIGS. 3B and 3C, inner tube 44 of the ASU has two separate longitudinal lumens 66a and 66b. The smaller lumen 66a may accommodate a conventional endoscope EN shown in phantom in FIG. 3B, e.g. about 25 mm in diameter, for direct visualization and monitoring of the particular procedure. The larger lumen, 66b, may carry various elongated flexible devices such as TIA 6 to be described for performing selected extra and intra-cardiac procedures.

Figure 4A:
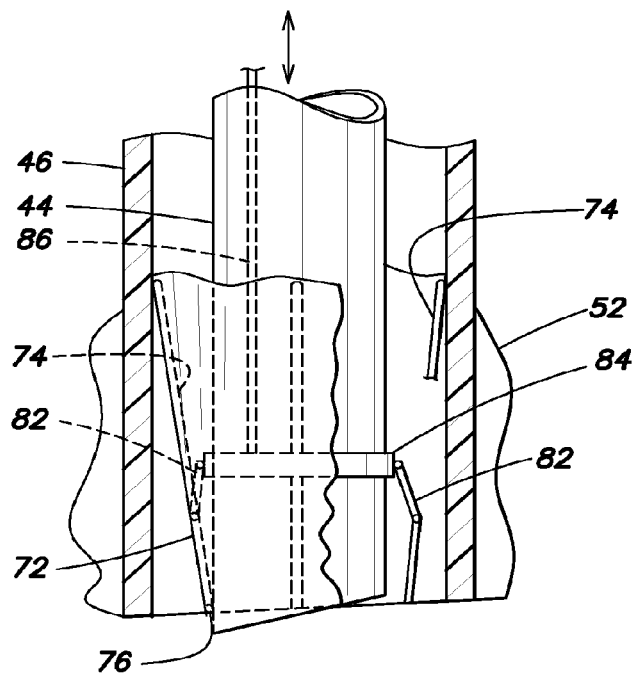
FIGS. 4A to 4C are fragmentary sectional views with parts in elevation showing the operation of the ASU.
Figure 4B:
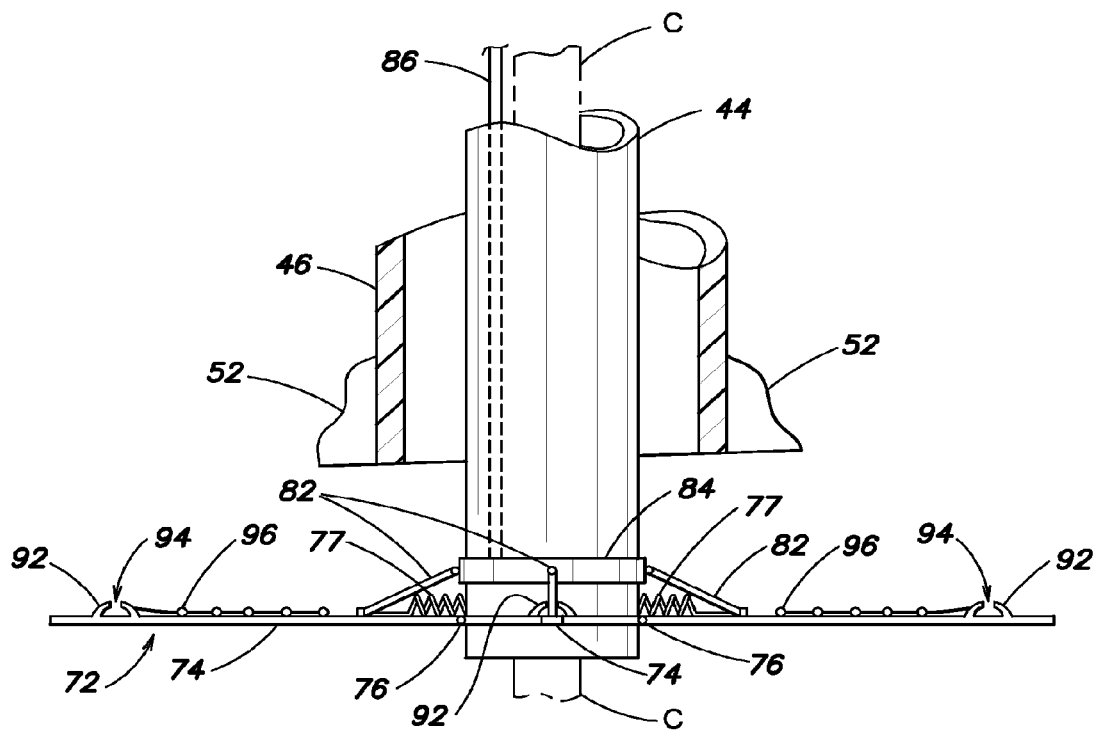

Referring now to FIGS. 3A, 4A and 4B, an umbrella 72 is provided at the distal end of tube 44 of ASU 4. The umbrella comprises a plurality, herein four, but more preferably six to eight, of flexible resilient radially arranged wires or stays 74 whose distal ends are hinged at 76 to the distal end of the tube 44 and flexible sheet material 78 extends between the stays. A corresponding plurality of struts 82 are hinged at both ends Is between stays 74 and a ring 84 encircling tube 44 so that by sliding ring 84 along tube 44, the umbrella 72 can be moved between a retracted position shown in FIGS. 3A and 4A and an extended position illustrated in FIG. 4B. The umbrella may be moved between its two positions by axially shifting a relatively stiff wire 86 extending from the ring to the proximal end of tube 44.

If desired, the stay hinges 76 may be spring loaded by springs 77 as shown in FIG. 4B so that umbrella 72 automatically opens when tube 44 is shifted axially until the umbrella clears the distal end of outer tube 46 as shown in FIG. 4B. Pulling on wire 86 will close the umbrella so that it can be retracted back into the outer tube 46 at the end of the procedure.

As seen from FIG. 4B, small knobs 92, each having a small recess 94 for capturing hooks 54b at the distal ends of needles 54 (FIG. 3A), are removably secured to stays 74. These knobs 92 are attached to the ends of suture threads 96 coiled up inside umbrella 72, each thread 96 being attached at its opposite ends to two adjacent knobs 92. This allows the formation of a purse string suture around the distal end of the ASU 42 after penetration through the wall Ew of the esophagus E.

Preferably, the distal ends of tubes 44 and 46 of ASU 42 are beveled as shown in FIGS. 4A and 4B to facilitate penetration of the esophageal wall Ew by penetration means C inserted into the ASU through lumen 66b thereof as shown in phantom in FIG. 4B. Such penetration means may consist of a needle with an overlying dilator, a conventional surgical blade, laser blade or other such means at the end of a probe or catheter introduced into lumen 66b. Preferably, the distal end of such means is beveled in line with the distal end of the ASU tubes.

Figure 4C:
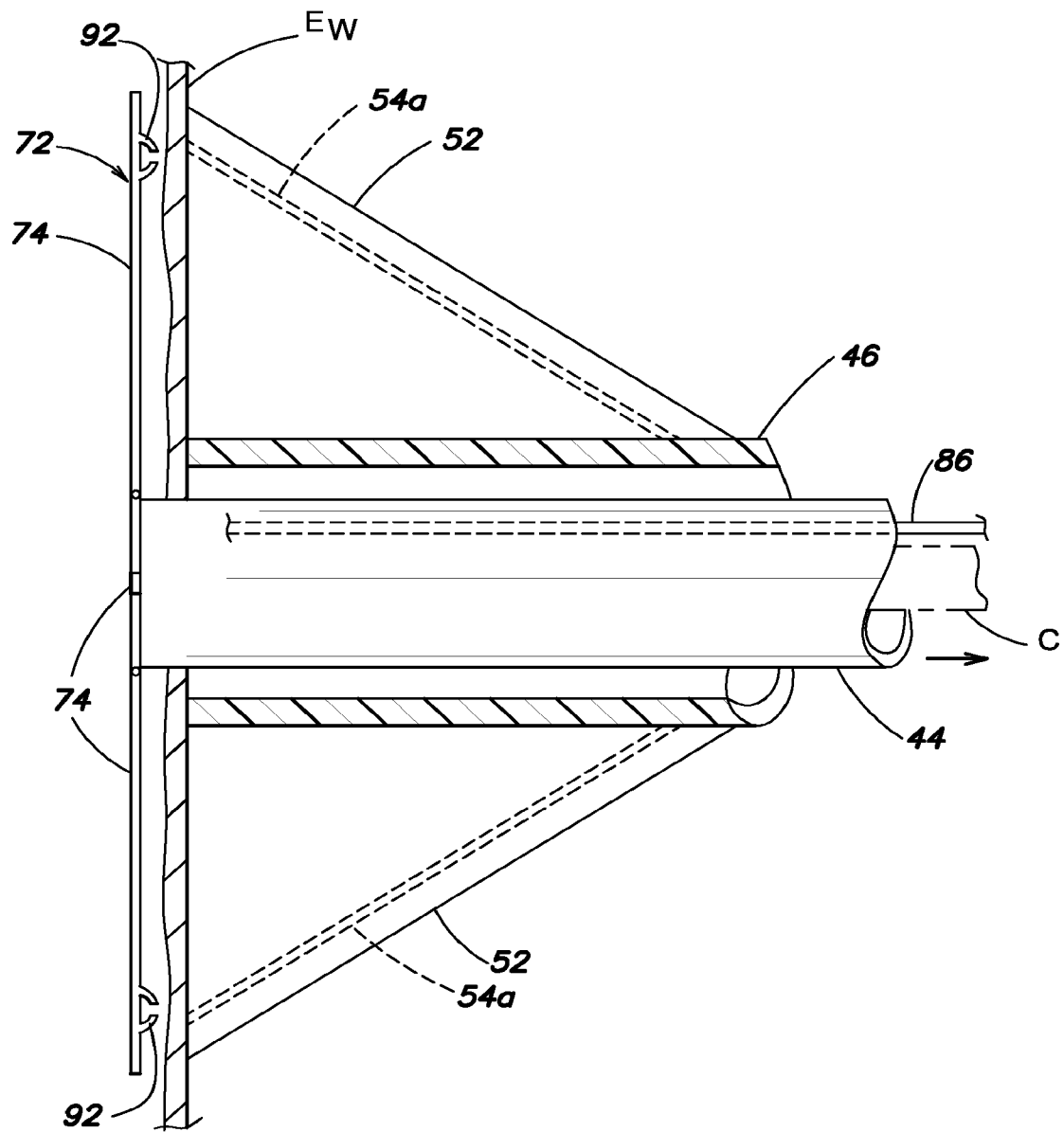

As best shown in FIG. 4C, after the distal ends of the penetration means C has cut through the esophageal wall Ew at opening O, the distal end of tube 46 with its flaps 52 extended may be butted adjacent that wall and the inner tube 44 extended until the umbrella 72 at its distal end clears the wall opening O. At that point, the umbrella may be opened and the tube 44 retracted so that the esophageal wall Ew is clamped between the flaps 52 and the umbrella 72 all around the wall opening O, all as shown in that drawing figure.

3) The Transesophageal Intercardiac Access (TIA) 6

Figure 5A:
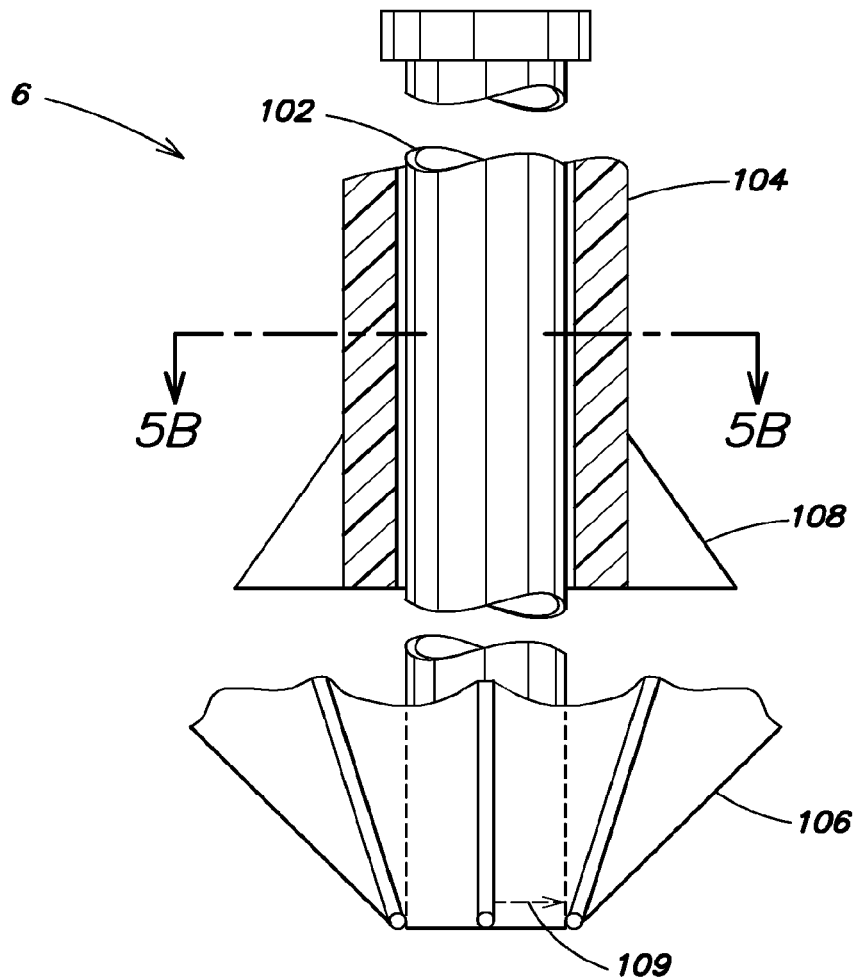
FIG. 5A is a view similar to FIG. 3A of the TIA component of the FIG. 1 apparatus.
Figure 5B:
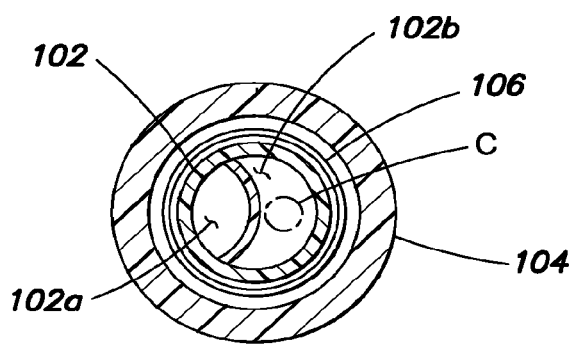
FIG. 5B is a sectional view taken at line 5B-5B of FIG. 5A.

Referring now to FIGS. 5A and 5B, TIA 6 comprises a long flexible catheter device that allows passage of elongated flexible devices into the interior of the heart to perform various procedures. The TIA is adapted to be introduced into the patient P via lumen 66b of the ASU 4. It comprises concentric inner and outer tubes 102 and 104, an umbrella 106 being present at the distal end of the former tube and flaps 108 being formed at the same end of the latter tube. In other words, TIA 6 is similar to ASU 4, and it functions in the same way to penetrate and seal the pericardium PC (FIG. 1) or a wall of the patient's heart H. Alternatively, other sealing means such as an inflatable balloon or double balloons may be used at the pericardium PC or the heart wall.

The TIA has a plurality of lumens 102a and 102b to accommodate another penetration means C as shown in FIG. 5B. TIA 6 may also include a hemostatic valve 109 to prevent backflow of blood in tube 102 after penetration of heart H.

Figure 6:
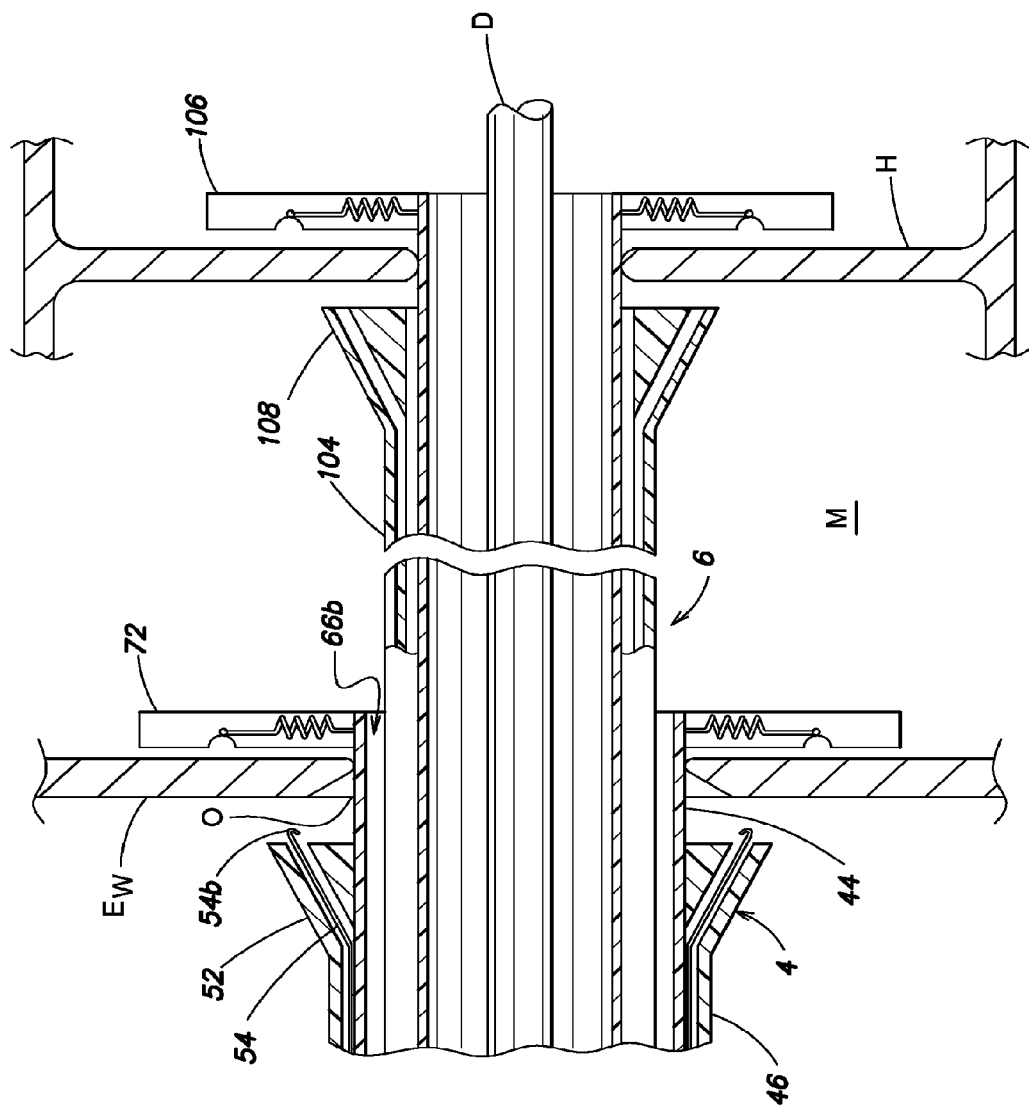
FIG. 6 is a view similar to FIG. 4C showing the TIA accessing the heart.

We will now describe the apparatus as it might be used to access the human beating heart. For this, TIA 6 may be extended from the intraesophageal position inside the lumen of the AMU 2 through the access side unit ASU 4. This allows the TIA to be positioned inside a cardiac chamber of heart H, preferably the left atrium as shown in FIG. 6. Advantageously, and according to a preferred embodiment of the invention, the patient is put only on conscious sedation, as general anesthesia may not be required for creating the transesophageal intracardiac access. The patient may or may not receive antibiotic premedication prior to the procedure depending on the risk stratification of the patient and procedure.

For this procedure, the AMU 2 is passed down the esophagus E to a suitable position so that the AEF is positioned behind a cardiac chamber, preferably the left atrium. The position of the AEF 18 can be determined by transesophageal ultrasound scanning or fluoroscopy. The above-mentioned irrigation-suction channels 34, 38 on the outside surface of the AMU are used to spray the esophageal mucosa on a large circumferential length with alternating rounds of saline and a suitable topical antiseptic for cleansing purposes. The double-layered ILL 12 is inflated with saline or a suitable fluid media to enhance the interface between the transesophageal probe and the heart for better ultrasound resolution. The outside balloon 24 of the AMU 2 is inflated with saline or any other enhancing ultrasound interface, against the inner aspect of the esophageal lumen. This creates a large area of circumferential pressure above and below the AEF 18 and prevents leakage from around the AEF. The channels 34, 38 are active throughout the procedure for constant cleansing and suction of the esophageal lumen and to provide negative vacuum pressure to ensure close approximation of the outside surface of inflated AMU balloon 24 to the inner surface of the esophageal mucosa.

By applying negative vacuum pressure to the SL 32 of the AMU 2, the area around the AEF 18 is approximated to the inner esophageal wall and provides continuous suctioning of any leaks that escape to the AEF. Thus, the AMU isolates a segment in the esophageal lumen behind a chamber in the heart, and allows the inserted devices to penetrate and create an access across the esophageal wall under sterile conditions.

According to the invention, the opening O is formed in an area of the esophageal wall Ew opposite the AEF. This may be accomplished by a cutting means such as an endoscopic cutting or penetration device, obturator, hollow cutting needle, electrosurgical blade, laser blade or similar means. In a preferred embodiment of the invention, a cutting hollow needle with an overlaying dilator sheath is positioned in the inner tube 44 of the ASU 4, which allows the ASU to slide out of the penetration site in the esophageal wall Ew into the posterior mediastinum M. After penetration and dilatation of the exit site, the needle and the dilator may be withdrawn to outside the patient's body. Advantageously, the penetration process through the esophageal wall is visually monitored through an endoscope EN in one of the lumens 66a, 66b of the ASU.

The invention method further entails the formation of a sealing mechanism after penetration into the esophageal wall. This can be an inflatable balloon, longitudinally expanding distal end of the ASU or a flange. In a preferred embodiment of the invention, the distal end of the ASU carries the umbrella-like device 72, as shown in FIG. 6, which is deployed after penetration to prevent any micro-leaking from the esophagus into the posterior mediastinum M. The structure of the umbrella of the ASU is similar to the TIA retractable umbrella mechanism. The sheet material 78 around the umbrella wires 74 isolates the opening O throughout the procedure. The umbrella 72 also allows the application of a purse string suture around the ASU exit, which is tightened to seal the penetration site in the esophageal wall and prepares for closing the site after the completion of the procedure. By pulling back the AMU, and with the aid of the vacuum suction pressure inside the SL around the AEF, the portion of the esophageal wall around the penetration site is displaced away from the posterior aspect of the heart. This space allows more room in the posterior mediastinum M for the devices described herein.

Still referring to FIG. 6, after establishment of the access in the posterior mediastinum, the TIA 6 is passed down the larger lumen 66b of the ASU 4 from outside the body to a position behind a chamber of the heart H. An endoscope EN in the smaller lumen 66a of the ASU allows for visual monitoring of the procedure. The TIA is used to pass flexible, longitudinal, tubular surgical devices D to perform procedures from this retrocardiac position.

Figure 7:
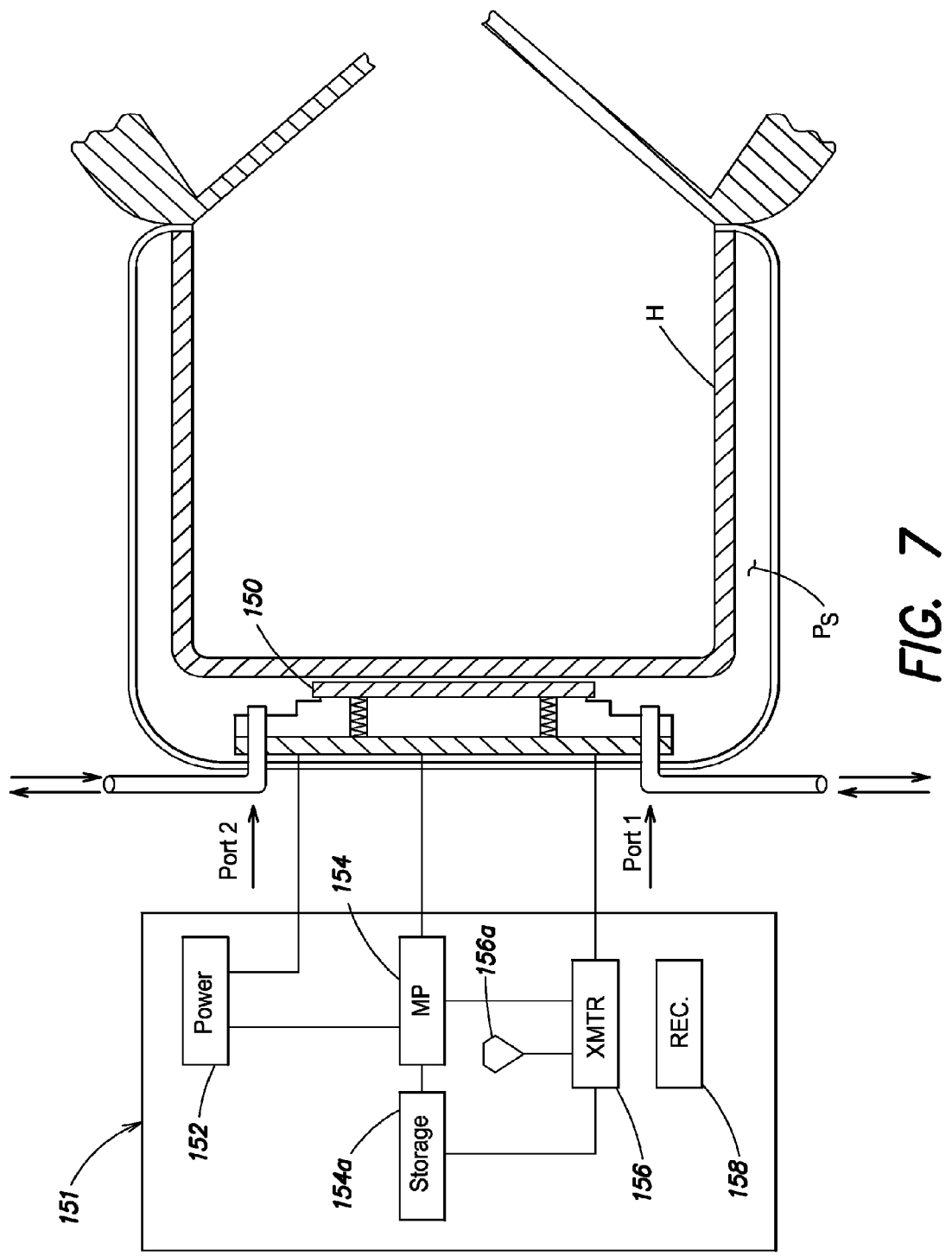
FIG. 7 is a diagrammatic view of the FIG. 1 apparatus used to monitor blood pressure.

In one embodiment of the invention, a diaphragm pressure sensor 150 of a suitable size is inserted through the TIA 6 into the pericardial space P.sub.s behind a cardiac chamber for acute and chronic data recording; see FIG. 7. The sensor measures the pressure inside a cardiac chamber of heart H through changes of the chamber wall tension. The sensor can sense and generate a signal for pericardial mapping and ablation. It is used as a vehicle for measuring vital data and substance delivery into the pericardial space, including temperature, pericardial fluid analysis, acute or chronic drug delivery, implantation of cells for angiogenesis or myogenesis, and the like.

The sensor 150 is connected to a hub 151 that contains a power unit 152, a microprocessor 154 including data storage 154a for data acquisition and analysis, and a transmitting unit 156 including an antenna 156a to send data to an outside receiver unit 158 either in a wired or preferably wireless fashion. The hub is placed either in a suitable area in the pericardial space P.sub.s such as the oblique sinus of the heart, or in the posterior mediastinum.

After insertion of the sensor 150 in the pericardium, the penetration site may be sealed around the wires that connect the sensor to the hub to create a closed space around the sensor to improve the sensitivity of the sensor diaphragm in measuring the cardiac chamber wall tension. The sealing means of the pericardial tissues are delivered through the TIA 6 and involve direct suturing, stapling or applying glue to the edges. The sealing positioning and manipulation of the sensor may be done under direct visual monitoring through an endoscope E.sub.N in the smaller lumen 66a of the ASU 4 (FIG. 3).

After implanting the sensor into the pericardial space and securing the penetration site, the TIA is withdrawn inside the larger lumen 66b of the ASU 4. The umbrella 72 around the distal end of the ASU is retracted to the non-deployed position and the ASU is withdrawn to the TAL 16 of the AMU 2. The purse string sutures applied to the esophageal wall around the esophageal opening O are pulled tight to close that penetration and draw the edges together. Glue can be applied to the inner aspect of the suture line to secure the seal. After completion of the procedure, the ASU 4 is withdrawn outside the body, the balloon of the AMU 2 is deflated and the AMU is withdrawn outside the body. According to the invention, the above method is completed without surgical incisions in the chest wall, without general anesthesia, and while the heart is beating.

In a second aspect of the invention, my method and apparatus may be used to repair a septal defect in the heart. In this event, the patient is sedated prior to the procedure, the esophageal mucosa is prepared and sterilized by means of the irrigation-suction channels of the AMU 2 which is positioned at a suitable location behind a cardiac chamber as described above. The balloon 24 of the AMU 2 is inflated to seal the esophageal lumen above and below the AEF. An ultrasound probe is then passed down the ILL 12 of the AMU for scanning during the procedure.

A penetration is made in the esophageal wall Ew behind a cardiac chamber preferably the left atrium to allow the ASU 4 to be positioned in the posterior mediastinum. The penetration can be done using a surgical blade, a hollow needle, radio frequency or a laser. The umbrella 72 on the distal end of the ASU is deployed to prevent leaking and to apply purse string sutures around the penetration site. A flexible endoscope EN is passed down the smaller lumen 66a of the ASU for direct visualization during the procedure. The larger lumen 66b of the ASU is used to pass penetration means to open through the pericardium and the muscular wall of a cardiac chamber. The penetration can be done using a surgical blade, a hollow needle, radio frequency or laser. The TIA 6 is then passed down the larger lumen of the ASU into the penetration site of the cardiac wall and inside the cardiac chamber. The umbrella 106 on the distal end of the TIA is then deployed to prevent leaking and to apply purse string sutures around the penetration site.

An intracardiac ultrasound probe may be passed down the lumen of the TIA 6 to visualize the septal defect and the image created by the intracardiac probe can be coupled to the transesophageal probe to create a stereoscopic 3D image from two positions. Other methods of intracardiac monitoring of the procedure employ an endoscope with a translucent interface over its distal lenses, an intracardiac angioscope introduced via a blood vessel or fluoroscopy. After accurate localization and assessment of the septal defect, a flexible purse-string suturing device (FPSS) similar to TIA 6 and carrying an intracardiac image acquisition probe in its lumen may be passed down the lumen of the TIA to the septal defect location. The positioning of the FPSS is accurately achieved under dual monitoring from the transesophageal and intracardiac probes 4 and 6, respectively.

After the FPSS is passed across the septal defect, the umbrella at the distal end thereof is deployed. The wires of the umbrella are flat with the surface of the septum. The outer sheath of the FPSS is moved forward to a designated position on the inner lumen of the FPSS and the enclosed needles are radially expanded and pushed forward as described above to penetrate the septal wall around the defect. The tips of the needles engage the thread knobs on the wires of the umbrella on the other side of the defect. By drawing back the outer sheath of the FPSS as described above for the TIA, the length of thread connecting two adjacent knobs is pulled out around the defect in a circular fashion and all the way from the defect to outside the body. The proximal ends of the threads are connected together extracorporeally either by direct knotting or by joining the ends inside a Vicryl cylinder. The threads are tensioned thus creating a purse string suture around the septal defect. A knot is formed between the two ends and pushed down the lumen of the TIA to close the defect in a circumferential pattern. The ends are then cut using flexible endoscopic scissors. The closure of the defect may be examined using the dual ultrasound imaging or direct visualization with an intracardiac scope or fluoroscope.

Other methods of repairing the septal defect already know in the art may be used through the lumen of the TIA. This includes applying a natural or artificial biocompatible material such as a patch to cover the defect. The natural material can be a piece of the posterior pericardium harvested through the TIA lumen.

Upon closure of the defect, the FPSS is withdrawn outside the body. The umbrella at the distal end of the TIA is retracted to a non-deployed position by applying tension on its control wire. The TIA is then withdrawn back into the lumen of the ASU 4 while drawing back the two ends of the suture thread. This tightens the purse string suture around the penetration site in the wall of the left atrium. The two ends are knotted together either extra or intracorporeally and pushed down the lumen of the ASU to close the penetration site. An endoscopic flexible scissors may be used to trim the ends of the knotted thread. Other methods of closing the defect can be used including stapling or applying fibrin glue to the edges. The closure of the penetration in the cardiac chamber wall is done under direct visualization through the endoscope inside the smaller lumen of the ASU 4.

The ASU is then withdrawn back inside the lumen of the AMU, and the penetration site in the esophageal wall is closed in a similar fashion to the cardiac wall. The balloon around the AMU may then be deflated and the device withdrawn outside the body.

In a further aspect of the invention, method and apparatus are provided for performing transesophageal electrophysiological procedures inside the heart.

The electrophysiological studies are procedures to diagnose and treat various types of cardiac dysrrhythmias including atrial, junctional, supraventricular and ventricular tachycardias. The electrophysiological procedures depend on two processes, namely electrical mapping which accounts for accurately defining the diseased tissue by a process called mapping and the second is ablation which is destroying temporarily or permanently the responsible tissue.

My techniques provide for precise and accurate performance of both aspects of electrophysiological procedures by accessing the pericardial, extra and intracardiac lumens of the heart through the transesophageal access device described above. Currently, such techniques are performed through the transvascular approach with puncture to the inter-atrial septum in many cases, or through open thoracotomy if more precision and larger areas of ablation are needed. Both methods have their disadvantages as mentioned at the outset. The above described transesophageal approach has the advantage of being minimally invasive similar to the transvascular approach and, meanwhile, allows for the performance of large-scale, accurate and easily controlled electrophysiological studies without the need for opening the chest wall. The electrophysiological technique according to the invention utilizes a transesophageal electrophysiological (TEEP) device 170 shown in FIGS. 8A to 8E.

4) The TEEP Device 170

The TEEP device 170 comprises an elongated flexible tube 172 that fits into the inner lumen of the ASU 4 or TIA 6. The lumen of the TEEP device contains an image-acquiring probe 174 for placement and monitoring of the procedure. The distal end of the TEEP device may carry an array of wires 176 that can be deployed radially in various shapes depending on the geometry of the tissue surface to be mapped or ablated. The wires are connected together with one or more circular sets of wires 178. Both the radially and transversely arranged wires make a net of wires similar to a spider web. Each of the net wires 176, 178 carries one or a plurality of electrodes or fiber-optic buds 182 mounted to its outer surface. These electrodes and fiber-optic buds arranged on the net of wires allow for a large area of precise mapping and ablation. The spider net wire arrangement is carried on the distal end of the TEEP device 170 in a non-deployed state for introduction through the access device 4 or 6. The fiber-optic buds on the wire array can be connected to a fiber-optic coupler that can transmit laser energy from a laser generator (not shown).

After the wire net array is deployed in the desired lumen, and by applying tension on the device, the array acquires the shape and the orientation of the inner aspect of the specified lumen. The electrodes are proximally connected to an electrical coupling device which, in turn, is connected to an ablation device (not shown), e.g., laser, radio frequency or microwave generator and also a sensing device (not shown) like an electro-cardiogram machine. The TEEP device 170 may be introduced through the lumen of the TIA 6 into a cardiac chamber of heart H, for example the left atrium. The imaging probe 174 in the lumen of the TEEP device may be passed through the lumen of the TEEP device and into the lumen of the cardiac chamber to allow for monitoring of the procedure and precise positioning of the wire array. The wires are deployed to the specified shape based on the internal geometry of the cardiac chamber. By applying tension on the TEEP device, the electrode buds 182 are positioned against the interior wall of the chamber to perform the specified electrophysiological study. The electrical potential difference between the spatially spread apart electrode buds 182 on the wire spider net array can be measured for any selected electrodes for accurate cardiac mapping. The use of such an array of electrodes helps to define the diseased tissue pathways in the chamber wall with precision. The wide lumen of the transesophageal intracardiac access (TIA) 6 allows for the use of larger electrodes or a linear laser which may also be used to transmit laser, microwave or a radiofrequency stream through the fiber-optic array or through one or more electrodes for highly selective, synchronous tissue ablation. This obviates the need for point-to-point electrical mapping and ablation currently used via the transvascular approach, which consumes lot of time and lacks precision due to the presence of intracardiac blood currents. Also, the above method of the invention creates a linear ablation line as it uses simultaneous adjacent electrodes mounted to the wire net array or continuous linear laser ablation.

Figure 8A:
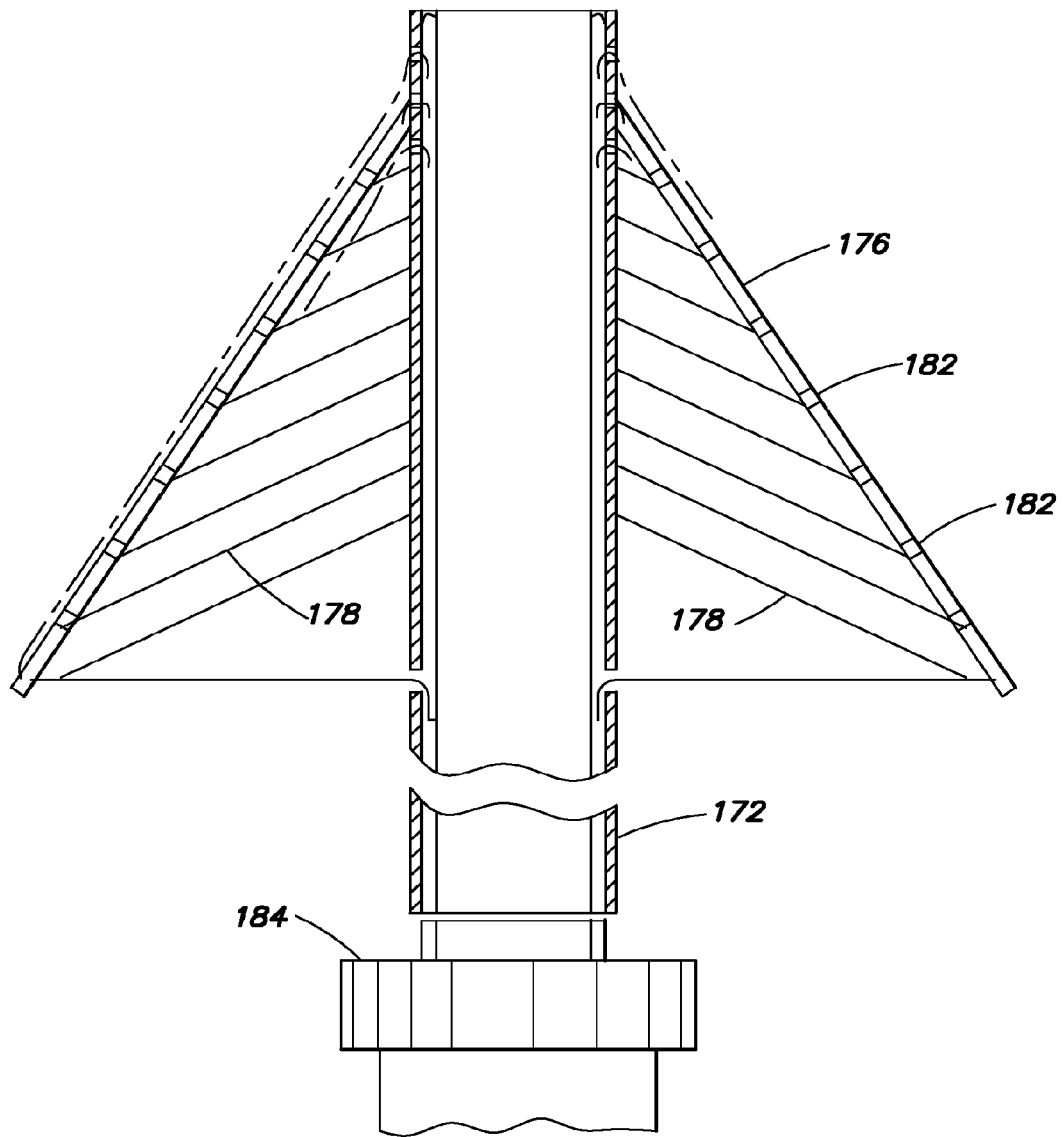
FIGS. 8A to 8E are similar views showing the apparatus used to repair a heart defect.
Figure 8B:
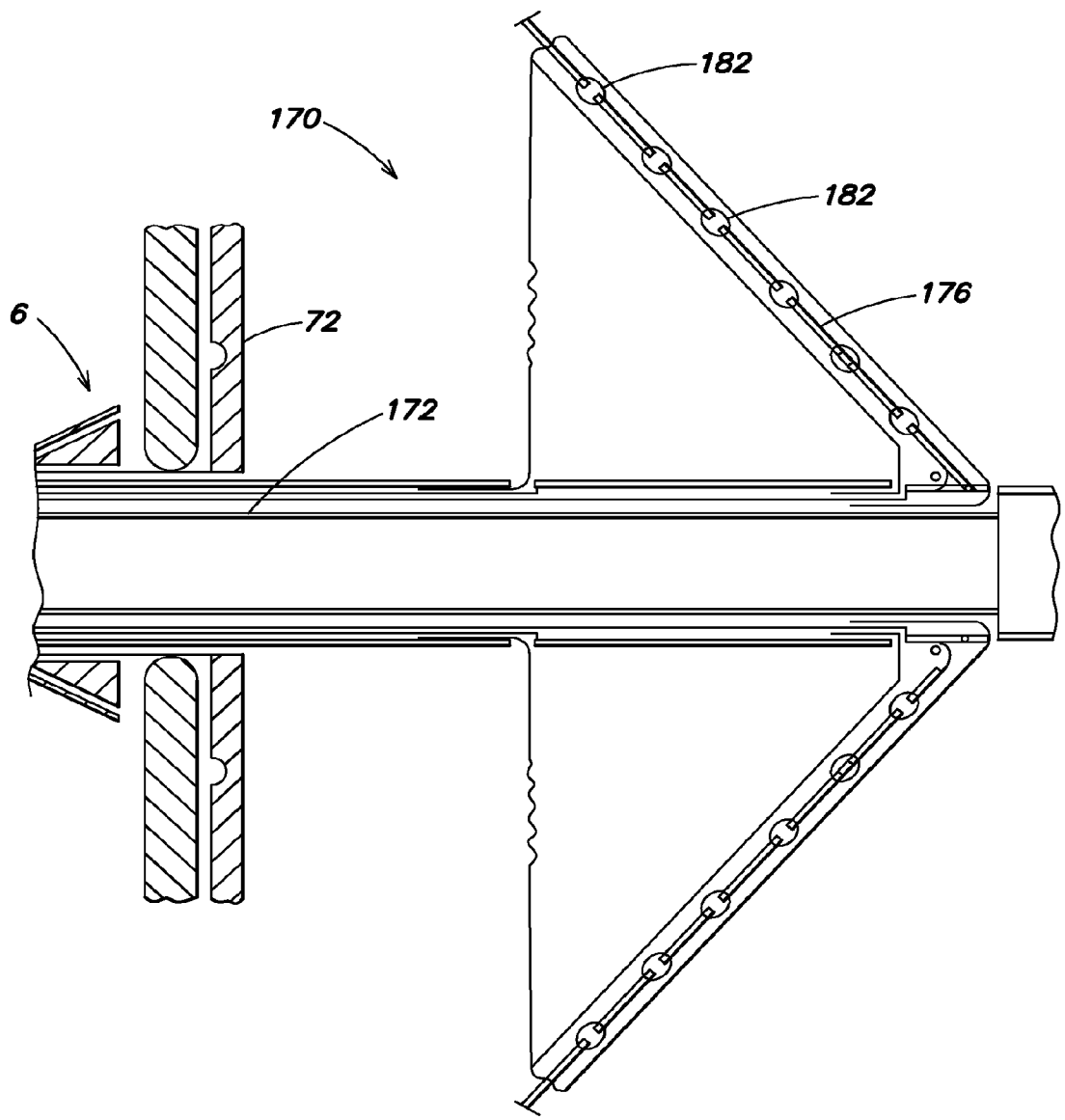
Figure 8C:
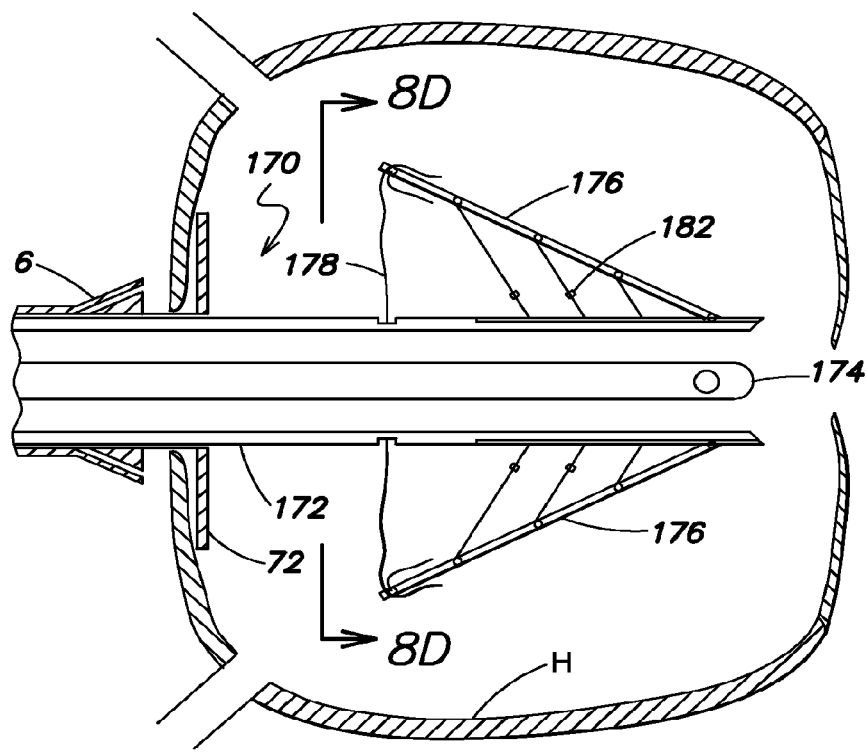
Figure 8D:
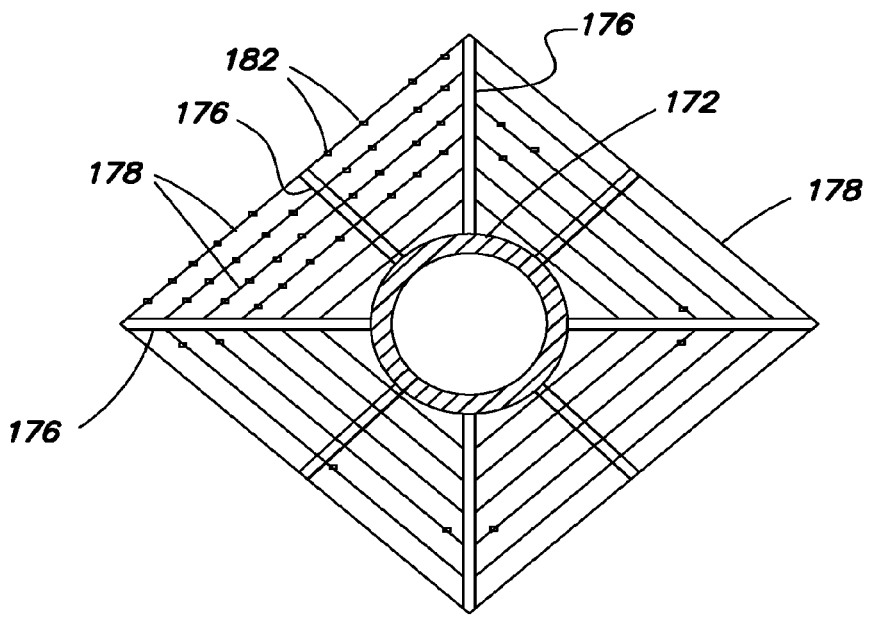
Figure 8E:
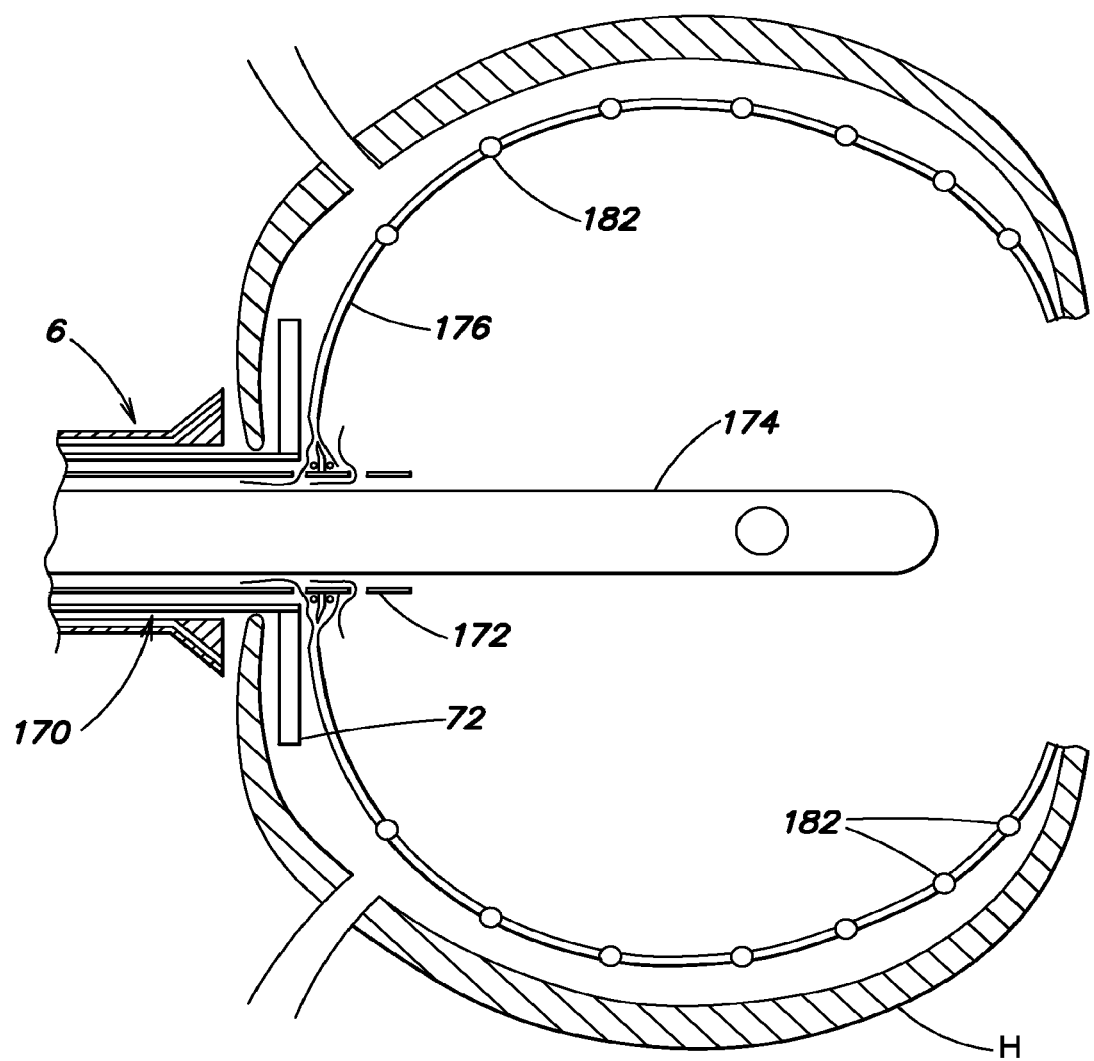

In a further embodiment of the invention, the wire array on the distal end of the TEEP device 170 may be made of any collapsible structure such as a contractile frame, inflatable balloon, or expanding wire basket. The collapsible structure is controlled by a proximal actuator 184 (FIG. 8A) of the TEEP device to control the deployment of a certain configuration of the collapsible array. This allows for selected electrodes or fiber-optic buds 182 on the array configuration to be positioned in a three-dimensional pattern against the inner aspect of the cardiac chamber wall as shown in FIG. 8E, thus facilitating the process of simultaneous mapping and ablation of a large area of the wall while the TEEP device 170 is in a fixed position and without the need to move the electrodes.

The short length and wide diameter of the TEEP device create efficient delivery of force and precision to the electrode array at the distal end of the device and allow for accurate controlled positioning of electrodes against various geometric shapes of a cardiac chamber. The wide diameter of the lumen of the TEEP device also allows for the use of larger and more numerous electrodes than what is currently used in the transvascular approach. It also allows the use of a linear laser that needs a wide lumen for laser fiber-optics. Hence, it allows for the delivery of more energy, the creation of more linear lesions and simultaneous ablation of a large area of the cardiac wall without moving the electrodes, fiber-optic buds or the device.

In one electrophysiological procedure, the TEEP device 170 is introduced 20 through the TIA 6 into a chamber of the heart H as described above. The spider web-shaped wire array at the distal end of the TEEP device carries a plurality of mounted electrodes. The array is collapsible and can be controlled by the actuator 184 from outside to permit selective deployment of a certain array configuration. The electrode buds 182 on the array are connected to an electrical coupler so that each electrode has a separate point of connection on the coupler with reference to its position on the array. With the aid of the image-acquiring probe 174, the actuator is used to precisely position a certain configuration of the electrode array against a part of the inner wall of the cardiac chamber as seen in FIG. 8E. The deployment of the resilient spider web-shaped wire array creates a three-dimensional configuration that accurately follows the inner definitions and details of a cardiac chamber. By applying tension on the TEEP device 170, this three-dimensional configuration is tightly positioned against the chamber wall and maintains its shape against the intracardiac blood flow currents. The electrical potential difference between any of the electrodes can be measured for mapping of the cardiac chamber. After defining the aberrant conduction tissue, a suitable amount of energy is delivered from the radio frequency or microwave generator to the electrodes defining the pathologic pathway.

Introducing the TEEP device in either the left or right atrium from a transesophageal position allows for performing the intracardiac electrophysiological procedures of the invention. The ventricles are accessed through the atrioventricular valves after the intra-atrial positioning of the device. The inter-atrial septum may be punctured to permit moving the device from one atrium to the other, but advantageously the TEEP device can be easily passed from the transesophageal position to the left atrium directly without the need to go through the right atrium as in the currently used transvascular technique.

In a second method of carrying out the electrophysiological procedures of the invention, the TEEP device is introduced to the oblique sinus of the pericardium for pericardial mapping and ablation. The space of the oblique sinus, which allows the passage of two fingers, is large enough to accommodate an array or frame of wires shaped to fit in the pericardial space around the heart. The actuator 184 on the proximal end of the TEEP device 170 is used to control the shape of the wire array in the pericardial space. Alternatively, the lumen of the TEEP device may be used to pass one or more wires to the pericardial space with one or more electrodes mounted on the outer surfaces of the wires. The wires can be moved freely around the heart for mapping or ablation procedures.

In a further embodiment of the invention, extracardiac mapping and ablation can be performed through the introduction of electrodes and laser probes of suitable diameter through ports 1 and 2 in pressure sensor 150 in FIG. 7 from a transesophageal position behind the heart to sense for aberrant pathways and to deliver linear laser energy to certain areas on the outside wall of a cardiac chamber without the need to penetrate inside the heart.

The invention may also be used to provide a unique combination of extra and intracardiac positions that allow for a variety of diagnostic and therapeutic procedures. In one exemplary aspect, the TEEP device 170 may be positioned inside the heart H for intracardiac mapping of aberrant pathways, while the extracardiac electrodes or laser probes are used to ablate the mapped pathological pathways. Alternatively, transesophageal extracardiac or pericardial mapping may be used to identify aberrant conduction tissues, while the TEEP device is used to deliver intracardiac radiofrequency, microwave or laser energy for ablation. In the latter example, a mapping device with sensing electrodes is introduced transesophageally to a position behind the heart through the smaller lumen of the ASU 4, for extracardiac surface mapping of aberrant pathways.

The TEEP device 170 of the invention is then introduced inside the heart to perform ablation based on the data acquired from the mapping device on the surface of the heart. This combined extra and intracardiac approach may be used to treat dysrrhythmias of complex nature like atrial fibrillation, ventricular or supraventricular tachyarrhythmias.

The combined extra and intracardiac mapping and ablation techniques of the invention are of special importance with regard to the Cox or "maze" procedure, which is of curative value in atrial fibrillation. In an exemplary procedure, the TEEP device 170 of the invention is introduced transesophageally inside the lumen of the left atrium across a penetration central to the entrance of the four pulmonary veins. The spider web-shaped wire array of the TEEP device is deployed to take the shape of the inner lumen of the left atrium. The electrodes and fiber-optic buds 182 on the wire array are positioned against the wall and stabilized in position by means of tension applied on the device. The spider web-shaped array is used to map the interior of the left atrial wall in a circular fashion around the openings of the four pulmonary veins. The electrodes or the fiber optic buds on the array may then be used to deliver linear energy that creates the "maze" lesions and directs the impulse from the sinoatrial node to the atriovenrticular node. Alternatively, ablation can be performed from an extra cardiac position by using ablation electrodes or preferably linear laser probes passed down the smaller lumen of the ASU 4 to a position behind the left atrium. The need for gross thoracotomy or multiple thoracoscopic opening to achieve access to the left heart limits the curative effect of the "maze" procedure. Thus, the invention provides a great advantage in the treatment of atrial fibrillation using the above-described technique without the need to open the chest wall.

The transesophageal access is also highly advantageous in creating a minimally invasive access to the posterior mediastinum, pericardial space and the interior of the heart while the heart is beating. It obviates the need for the traumatic tissue effect and morbidity that may result from gross or limited thoracotomy or cardioplegic arrest of the heart. The ability to acquire transesophageal and intracardiac ultrasound images plus direct endoscopic visualization and monitoring of the procedure makes the transesophageal access an easy, precise and safe approach to the posterior mediastinum and the inner and outer aspects of the heart.

A whole body of procedures can be performed using the invention devices and procedures to achieve simultaneous extra and intra-cardiac accesses. Besides the above mentioned exemplary embodiments that show the powerful ability of the transesophageal approach to access and precisely manipulate the heart, several other procedures may be performed including but not confined to cardiac valvular repair and manipulations, manipulation of mediastinal great vessels like pulmonary thrometectomy or aortic manipulations, repair of several types of cardiac congenital defects, intracardiac surgical or laser removal of thrombi, tumors, vegetations, or lesions, transmyocardial laser revascularization either from inside or outside the heart, biopsy of the heart, septal myectomy, the creation of combined stereoscopic ultrasound or endoscopic images of the heart from different positions, coronary revascularization or bypass techniques and other extra and intra cardiac procedures.

It will thus be seen that the objects set forth above are efficiently attained, and since certain changes may be made in the above method and constructions, it is intended that all matter contained in the above description or shown in the accompanying drawings shall be interpreted as illustrative and not in a limiting sense.

It is also to be understood that the following claims are intended to cover all of the generic features of the invention described herein.

What is claimed is:

1. A method of performing an intra-thoracic procedure, comprising:
   inserting one or more surgical instruments into a patient's esophagus so that the one or more surgical instruments are positioned within the patient's thoracic cavity;
   introducing a cutting device into the patient's esophagus so that a distal end of the cutting device is positioned within the patient's thoracic cavity;
   forming an opening in an esophageal wall with the cutting device thereby providing access to the patient's intra-thoracic cavity from the esophagus;
   establishing a seal around said opening to inhibit fluid leakage between the esophagus and the intra-thoracic cavity; and
   performing a surgical procedure in the intra-thoracic cavity using the one or more surgical devices.

2. The method according to claim 1, further comprising an act of passing a first monitoring device into the patient's esophagus to monitor the procedure.

3. The method according to claim 1, wherein the act of introducing the cutting device includes an act of passing the cutting device through the one or more surgical instruments so that the distal end of the cutting device is positioned within the patient's thoracic cavity.

4. The method according to claim 1, further comprising an act closing the opening in the esophageal wall upon conclusion of the intra-thoracic surgical procedure.

5. The method according to claim 4, wherein the act of closing the opening includes act of sealing the opening by performing at least one of: applying glue to the opening, suturing the opening, and applying a laser to seal the opening.

6. The method according to claim 1, wherein the act of establishing the seal around the opening includes an act of inflating at least one inflation member to seal a portion of the esophagus.

7. The method according to claim 6, wherein the act of establishing the seal includes inflating at least a second inflation member to provide an upper and lower seal in the esophagus.

8. A method for intra-thoracic surgery, comprising:
   inserting a first surgical device through a mouth of a patient into an esophagus of the patient;
   inserting an incising instrument into the esophagus through the first surgical device;
   manipulating the incising instrument from outside the patient to form a perforation in an internal wall of the esophagus opening into a thoracic cavity;
   moving a distal end of a second surgical device through said perforation;
   performing a surgical operation on the intra-thoracic organ by manipulating the second surgical device;
   closing said perforation; and
   withdrawing the second surgical device, the incising instrument and the first surgical device from the patient's esophagus.

9. The method according to claim 8, further comprising an act of establishing a seal around said opening to inhibit fluid leakage between the esophagus and the intra-thoracic cavity.

10. The method according to claim 9, wherein the act of establishing the seal around said opening includes an act of inflating at least one inflation member to seal a portion of the esophagus.

11. The method according to claim 10, wherein the act of establishing the seal includes inflating at least a second inflation member to provide an upper and lower seal in the esophagus.

12. The method according to claim 8, wherein the act of closing the perforation includes an act of sealing the opening by performing at least one of: applying glue to the opening, suturing the opening, and applying a laser to seal the opening.

13. A method for performing a minimally invasive surgical procedure, the method comprising:
   inserting a surgical device into a mouth of a patient;
   positioning the surgical device within a thoracic cavity of the patient within an esophagus;
   isolating a segment of the esophagus using the surgical device; and
   generating access to the thoracic cavity, using the surgical device, through the esophagus within the isolated segment.

14. The method according to claim 13, where in the act of generating includes an act of cutting an opening through the esophagus to generate access to the thoracic cavity.

15. The method according to claim 13, further comprising an act of passing a second surgical device through the opening.

16. The method according to claim 13, further comprising an act of performing surgery on an exterior or interior portion of a heart of the patient.

17. The method according to claim 13, wherein the act of isolating the segment of the esophagus includes an act of inflating at least one inflation member to seal a portion of the esophagus.

18. The method according to claim 17, wherein the act of isolating the segment of the esophagus includes an act of inflating at least a second inflation member to provide an upper and lower seal in the esophagus.

* * * * *